US006245562B1

(12) United States Patent
Dalla-Favera

(10) Patent No.: US 6,245,562 B1
(45) Date of Patent: Jun. 12, 2001

(54) IDENTIFICATION OF GENES ALTERED IN MULTIPLE MYELOMA

(75) Inventor: Riccardo Dalla-Favera, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 08/654,482

(22) Filed: May 28, 1996

(51) Int. Cl.$^7$ .......................... C07H 21/04; C07H 21/02; C12N 15/63; C12N 15/85
(52) U.S. Cl. .......................... 435/325; 435/6; 435/69.1; 435/320.1; 435/348; 435/410; 435/243; 536/23.1; 536/23.5; 536/23.52
(58) Field of Search .......................... 435/6, 69.1, 320.1, 435/325, 348, 410, 243; 536/23.1, 23.5, 23.52; 530/351

(56) References Cited

U.S. PATENT DOCUMENTS 5,891,666 * 4/1999 Matsuyama et al. ................ 435/69.1

OTHER PUBLICATIONS

Bakhshi, A. et al. (1985) *Cell* 41(3):889–906.
Cleary, M.L. and Sklar, J. (1985) *Proc. Natl. Acad. Sci. USA* 81(21):7439–7443.
Dalla–Favera, R. et al. (1982) *Proc. Natl. Acad. Sci. USA* 79(24):7824–7827.
Dewald, G.W. et al. (1985) *Blood* 66(2):380–390.
Driggers, P.H. et al. (1990) *Proc. Natl. Acad. Sci. USA* 87(10):3743–3747.
Eisenbeis, C.F. (1995) *Genes & Dev.* 9(11):1377–1387.
Eton, O. et al. (1989) *Leukemia* 3(10):729–735.
Feidler, W. et al (1992) *Br.J. Haematol.* 81(1):58–61.
Gould, J. et al. (1998) *Blood* 71(2):453–456.
Grant, C.E. et al. (1995) *Nucleic Acids Res.* 23(12):2137–2146.
Iida, S. et al. (1993) *Oncogene* 8(11):3085–3092.
Jernberg, H. et al. (1987) *Int. J. Cancer* 40(6):811–817.
Kozak, M. (1989) *J. Cell Biol.* 108(2):229–241.
Mazars, G–R. et al. (1992) *Oncogene* 7(5):1015–1018.
Motokura, T. et al. (1991) *Nature* 350(6318):512–515.
Rabbitts, T.H. (1994) *Nature* 372(6502):143–149.

Rabbitts, P.D. et al. (1988) *Oncogene* 3(1):99–103.
Rao, P.H. et al. (1994) *Cytogenet. Cell Genet.* 66(4):272–273.
Seto, M. et al. (1992) *Oncogene* 7(7):1401–1406.
Sun, Z. and Kitchingman, G.R. (1991) 1(5):347–355.
Taniwaki, M. et al. (1994) *Blood* 84(7):2283–2290.
Tsujimoto, Y. et al. (1985) *Nature* 315(6017):340–343.
Tsujimoto, Y. et al. (1984) *Science* 224(4656):1403–1406.
Veals, S.A. et al. (1992) *Mol. Cell Biol.* 12(8):3315–3324.
Weh, H.J. et al. (1993) *Eur. J. Cancer* 29A(9):1269–1273.
Yamagata, T. et al. (1996) *Mol. Cell. Biol.* 16(4):1283–1294.
Ye, B.H. et al. (1993) *Science* 262(5134):747–750.
Zhang, X–G, et al. (1994) *Blood* 83(12):3654–3663.
Matsuyama, T., et al., Molecular Cloning of LSIRF, A Lymphoid–Specific Member of the Interferon Regulatory Factor Family that Binds the Interferon–Stimulated Response Element (ISRE). *Nucleic Acids Reserch*. vol. 23(12):2127–2136 1995.*
Grossman et al, Allession No. U52682 on EMBL/GonBank/DDBJ Databases, Apr. 19, 1996.*

* cited by examiner

*Primary Examiner*—George C. Elliott
*Assistant Examiner*—Sean McGarry

(57) ABSTRACT

This invention provides a method of determining a chromosomal breakpoint in a subject suffering from multiple myeloma which comprises steps of: (a) obtaining a DNA sample from the subject suffering from multiple myeloma; (b) determining whether there is J and C disjunction in the immunoglobulin heavy chain gene in the obtained DNA sample; (c) obtaining a genomic library having clones which contain genomic DNA fragments from the DNA sample which shows positive J and C disjunction; (d) selecting and isolating clones of the obtained library which show positive hybridization with a probe which is capable of specifically hybridizing with the C but not the J region of the immunoglobulin heavy chain gene; (e) preparing fluorescent probes from the genomic DNA fragments of the isolated clones from step (d); (f) hybridizing said fluorescent probes with metaphase chromosomes; and (g) determining the identity of the chromosomes which are capable of hybridizing to said fluorescent probes, wherein the identification of a chromosome other than chromosome 14 would indicate that the chromosomal breakpoint is between chromosome 14 and the identified chromosome, thereby determining a chromosomal breakpoint in a subject suffering from multiple myeloma. This invention also provides the identified gene altered by a chromosomal breakpoint and various uses thereof.

14 Claims, 21 Drawing Sheets

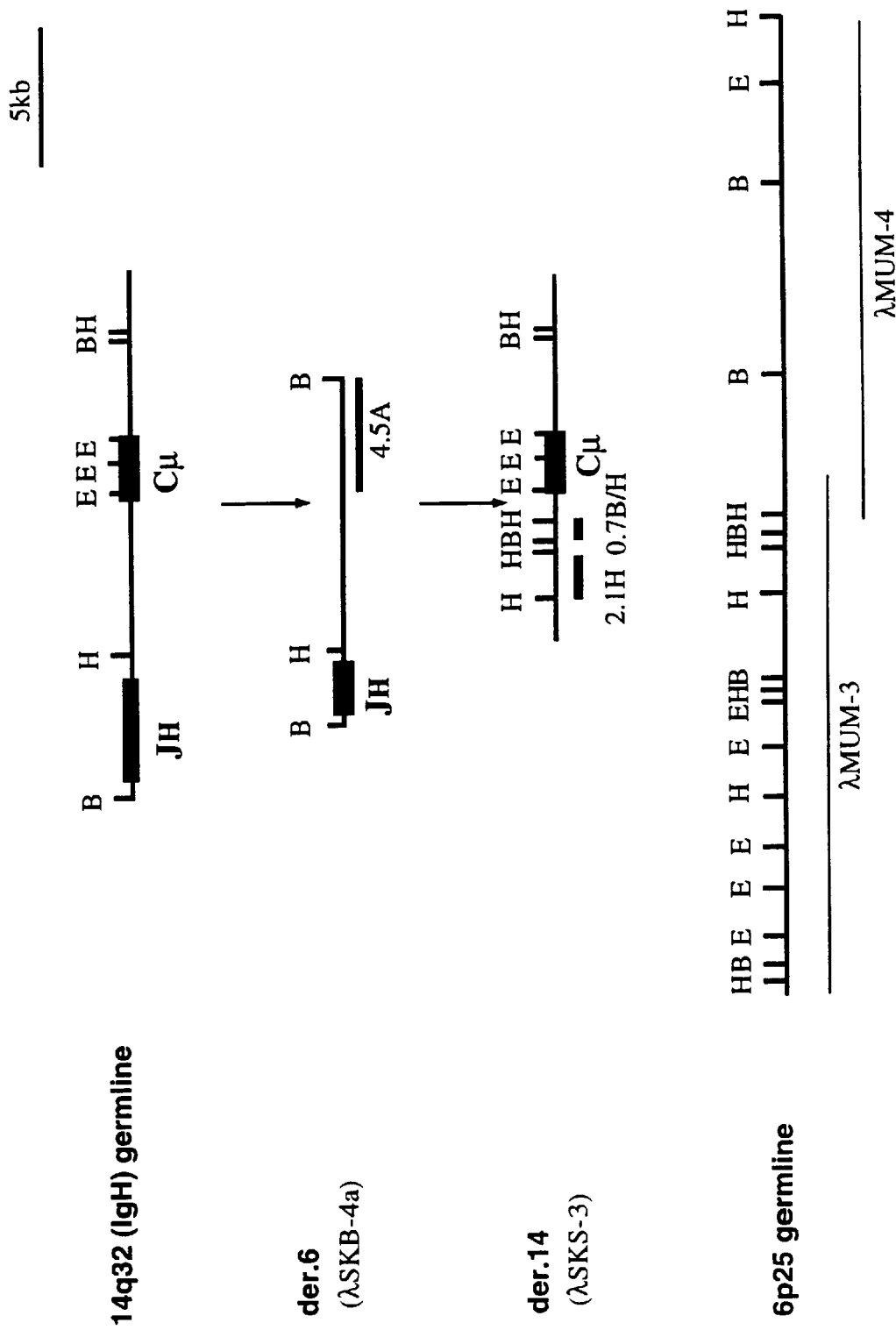

FIG. 2B

```
ch. 6    TTTTCTCTCTACAGTCACCTCCCTGTTTACCAAAGATAATCACAATAAGTCCAGTTTACTTACAAAACAAGTTTAGT
                                                             |||||||||||||||||||||||||||||||||||
der.6    TGGGCTCGGCC-TGGTGGGCAGCCACACAGCCGGGACGC-AGTAGTGAAAGTCCAGTTTACTTACAAAACAAGTTTAGT
         ||||||||||   |||||||||||||||||||||||||   ||||||||
ch.14    TGGGCTCGGCCTTGGTGGGCAGCCACAGCGGGACGCAAGTAGTGAGGGCACTCAGAACGCCACTCAGCCCCGACAG
         4400            4410           4420           4430           4440           4450           4460           4470 ch.6     TATTAGAGGAAACTAAAACTTCAGGATTCAGTCCAGATAATTTTTAAAAAACTCTAAAACAATGGACAGGGCTAGAAT
         |||||||||||||||||||||||||||||||||||                  |||||||||||||||||||||||||||
der.6    TATTAGAGGAAACTAAAACTTCAGGATTCAGCAGGGCATGAGGAGGCAGCTCCTCACCCTCCCTTTCTCTCTTTGTAC
         |||||||||||||||||||||||||||||||                      |||||||||||||||||||||||||||
ch.14    GGCACTCAGAACGCCACTCAGCCCCGACAGCCCCGACAGCCCCGACAGCCCCGACAGCTCCTCACCCTCCCTTTCTCTTTGT--
         4450           4460           4470           4480           4490           4500           4510
```

FIG. 3A
FIG. 3B
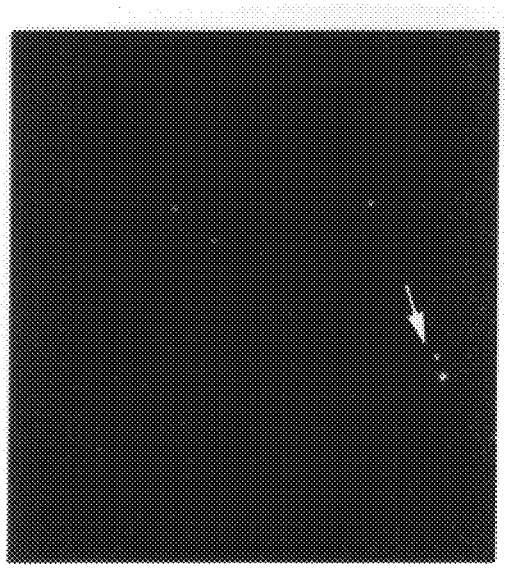
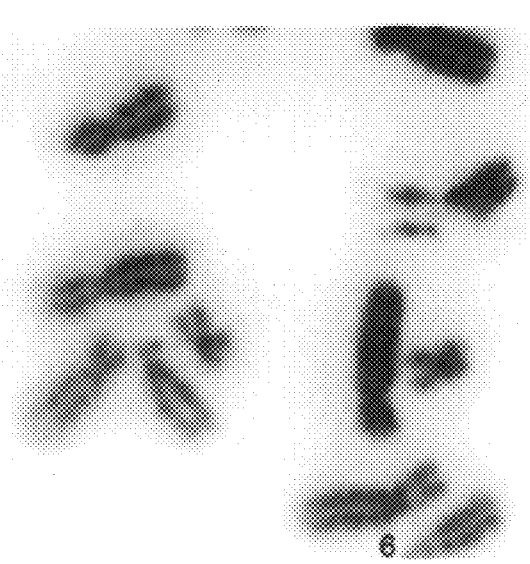
λMUM1-3

MUM1 cDNA RESTRICTION MAP

FIG. 5B-1

```
   1 GCCTGACCAA CATGGTAAAA CCCCATCTCT GCTAAAACTA CAAAAAATTA
  51 GCTGGATGTG GTGGCAGGGA ACCTGTCATC CCAGCTAGTT GGGAGACTGA
 101 GGCAGGAGAA TCGCTCGATC TTGGGACCCA CCGCTGCCCT CAGCTCCGAG
 151 TCCAGGGCGA GTGCAGAGCA CAGCGGGCGG AGGACCCCGG GCGCGGGCGC
 201 GGACGGCACG CGGGGCATGA ACCTGGAGGG CGGCGGCCGA GGCGGAGAGT
                          M  N  L  E  G   G  G  R   G  G  E  F
 251 TCGGCATGAG CGCGGTGAGC TGCGGCAACG GAAGCTCCG CCAGTGGCTG
      G  M  S   A  V  S    C  G  N      K  L  R   Q  W  L
 301 ATCGACCAGA TCGACAGCGG CAAGTACCCC GGGCTGGTGT GGGAGAACGA
      I  D  Q  I   D  S  G   K  Y  P   G  L  V  W   E  N  E
 351 GGAGAAGAGC ATCTTCCGCA TCCCCTGGAA GCACGCGGGC AAGCAGGACT
      E  K  S   I  F  R  I   P  W  K   H  A  G   K  Q  D  Y
 401 ACAACCGCGA GGAGGACGCC GCGCTCTTCA AGGCTTGGGC ACTGTTTAAA
      N  R  E   E  D  A   A  L  F  K   A  W  A   L  F  K
 451 GGAAAGTTCC GAGAAGGCAT CGACAAGCCG GACCCTCCCA CCTGGAAGAC
      G  K  F  R   E  G  I   D  K  P   D  P  P  T   W  K  T
 501 GCGCCTGCGG TGCGCTTTGA ACAAGAGCAA TGACTTTGAG GAACTGGTTG
      R  L  R   C  A  L  N   K  S  N   D  F  E   E  L  V  E
 551 AGCGGAGCCA GCTGGACATC TCAGACCCGT ACAAAGTGTA CAGGATTGTT
      R  S  Q   L  D  I   S  D  P  Y   K  V  Y   R  I  V
 601 CCTGAGGGAG CCAAAAAAGG AGCCAAGCAG CTCACCCTGG AGGACCCGCA
      P  E  G  A   K  K  G   A  K  Q   L  T  L  E   D  P  Q
 651 GATGTCCATG AGCCACCCCT ACACCATGAC AACGCCTTAC CCTTCGCTCC
      M  S  M   S  H  P  Y   T  M  T   T  P  Y   P  S  L  P
 701 CAGCCCAGCA GGTTCACAAC TACATGATGC CACCCCTCGA CCGAAGCTGG
      A  Q  Q   V  H  N   Y  M  M  P   P  L  D   R  S  W
 751 AGGGACTACG TCCCGGATCA GCCACACCCG GAAATCCCGT ACCAATGTCC
      R  D  Y  V   P  D  Q   P  H  P   E  I  P  Y   Q  C  P
 801 CATGACGTTT GGACCCCGCG GCCACCACTG GCAAGGCCCA GCTTGTGAAA
      M  T  F   G  P  R  G   H  H  W   Q  G  P   A  C  E  N
 851 ATGGTTGCCA GGTGACAGGA ACCTTTTATG CTTGTGCCCC ACCTGAGTCC
      G  C  Q   V  T  G   T  F  Y  A   C  A  P   P  E  S
 901 CAGGCTCCCG GAGTCCCCAC AGAGCCAAGC ATAAGGTCTG CCGAAGCCTT
      Q  A  P  G   V  P  T   E  P  S   I  R  S  A   E  A  L
 951 GGCGTTCTCA GACTGCCGGC TGCACATCTG CCTGTACTAC CGGGAAATCC
      A  F  S   D  C  R  L   H  I  C   L  Y  Y   R  E  I  L
1001 TCGTGAAGGA GCTGACCACG TCCAGCCCCG AGGGCTGCCG GATCTCCCAT
      V  K  E   L  T  T   S  S  P  E   G  C  R   I  S  H
1051 GGACATACGT ATGACGCCAG CAACCTGGAC CAGGTCCTGT TCCCCTACCC
      G  H  T  Y   D  A  S   N  L  D   Q  V  L  F   P  Y  P
1101 AGAGGACAAT GGCCACAGGA AAACATTGA GAACCTGCTG AGCCACCTGG
      E  D  N   G  H  R  K   N  I  E   N  L  L   S  H  L  E
```

(5B-1 - 5B-3) MUM1 cDNA NUCLEOTIDE SEQUENCE AND
CORRESPONDING AMINO ACIDS

FIG. 5B-2

```
1151 AGAGGGGCGT GGTCCTCTGG ATGGCCCCCG ACGGGCTCTA TGCGAAAAGA
      R  G  V    V  L  W    M  A  P  D    G  L  Y    A  K  R
1201 CTGTGCCAGA GCACGATCTA CTGGGACGGG CCCCTGGCGC TGTGCAACGA
      L  C  Q  S  T  I  Y    W  D  G    P  L  A  L    C  N  D
1251 CCGGCCCAAC AAACTGGAGA GAGACCAGAC CTGCAAGCTC TTTGACACAC
      R  P  N    K  L  E  R    D  Q  T    C  K  L    F  D  T  Q
1301 AGCAGTTCTT GTCAGAGCTG CAAGCGTTTG CTCACCACGG CCGCTCCCTG
      Q  F  L    S  E  L    Q  A  F  A    H  H  G    R  S  L
1351 CCAAGATTCC AGGTGACTCT ATGCTTTGGA GAGGAGTTTC CAGACCCTCA
      P  R  F  Q    V  T  L    C  F  G    E  E  F  P    D  P  Q
1401 GAGGCAAAGA AAGCTCATCA CAGCTCACGT AGAACCTCTG CTAGCCAGAC
      R  Q  R    K  L  I  T    A  H  V    E  P  L    L  A  R  Q
1451 AACTATATTA TTTTGCTCAA CAAAACAGTG GACATTTCCT GAGGGGCTAC
      L  Y  Y    F  A  Q    Q  N  S    G  H  F  L    R  G  Y
1501 GATTTACCAG AACACATCAG CAATCCAGAA GATTACCACA GATCTATCCG
      D  L  P  E    H  I  S    N  P  E    D  Y  H  R    S  I  R
1551 CCATTCCTCT ATTCAAGAAT GAAAAATGTC AAGATGAGTG GTTTTCTTTT
      H  S  S    I  Q  E  *
1601 TCCTTTTTTT TTTTTTTTTT TTTGATACGG AGATACGGGG TCTTGCTCTG
1651 TCTCCCAGGC TGGAGTGCAG TGACACAATC TCAGCTCACT GTGACCTCCG
1701 CCTCCTGGGT TCAAGAGACT CTCCTGCCTC AGCCTCCCTG GTAGCTGGGA
1751 TTACAGGTGT GAGCCACTGC ACCCACCCAA GACAAGTGAT TTTCATTGTA
1801 AATATTTGAC TTTAGTGAAA GCGTCCAATT GACTGCCCTC TTACTGTTTT
1851 GAGGAACTCA GAAGTGGAGA TTTCAGTTCA GCGGTTGAGG AGAATTGCGG
1901 CGAGACAAGC ATGGAAAATC AGTGACATCT GATTGGCAGA TGAGCTTATT
1951 TCAAAAGGAA GGGTGGCTTT GCATTTTCTT GTGTTCTGTA GACTGCCATC
2001 ATTGATGATC ACTGTGAAAA TTGACCAAGT GATGTGTTTA CATTTACTGA
2051 AATGCGCTCT TTAATTTGTT GTAGATTAGG TCTTGCTGGA AGACAGAGAA
2101 AACTTGCCTT TCAGTATTGA CACTGACTAG AGTGATGACT GCTTGTAGGT
2151 ATGTCTGTGC CATTTCTCAG GGAAGTAAGA TGTAAATTGA AGAAGCCTCA
2201 CACGTAAAAG AAATGTATTA ATGTATGTAG GAGCTGCAGT TCTTGTGGAA
2251 GACACTTGCT GAGTGAAGGA AATGAATCTT TGACTGAAGC CGTGCCTGTA
2301 GCCTTGGGGA GGCCCATCCC CCACCTGCCA GCGGTTTCCT GGTGTGGGTC
2351 CCTCTGCCCC ACCCTCCTTC CCATTGGCTT TCTCTCCTTG GCCTTTCCTG
2401 GAAGCCAGTT AGTAAACTTC CTATTTTCTT GAGTCAAAAA ACATGAGCGC
2451 TACTCTTGGA TGGGACATTT TTGTCTGTCC TACAATCTAG TAATGTCTAA
2501 GTAATGGTTA AGTTTTCTTG TTTCTGCATC TTTTTGACCC TCATTCTTTA
2551 GAGATGCTAA AATTCTTCGC ATAAAGAAGA AGAAATTAAG GAACATAAAT
2601 CTTAATACTT GAACTGTTGC CCTTCTGTCC AAGTACTTAA CTATCTGTTC
2651 CCTTCCTCTG TGCCACGCTC CTCTGTTTGT TTGGCTGTCC AGCGATCAGC
2701 CATGGCGACA CTAAAGGAGG AGGAGCCGGG GACTCCCAGG CTGGAGAGCA
2751 CTGCCAGGAC CCACCACTGG AAGCAGGATG GAGCTGACTA CGGAACTGCA
2801 CACTCAGTGG GCTGTTTCTG CTTATTTCAT CTGTTCTATG CTTCCTCGTG
2851 CCAATTATAG TTTGACAGGG CCTTAAAATT ACTTGGCTTT TTCCAAATGC
2901 TTCTATTTAT AGAAATCCCA AAGACCTCCA CTTGCTTAAG TATACCTATC
2951 ACTTACATTT TTGTGGTTTT GAGAAAGTAC AGCAGTAGAC TGGGGCGTCA
3001 CCTCCAGGCC GTTTCTCATA CTACAGGATA TTTACTATTA CTCCCAGGAT
```

FIG. 5B-3

```
3051  TCAGCAGAAG ATTGCGTTAG CTCTCAAATG TGTGTTCCTG CTTTTCTAAT
3101  GGATATTTTA AATTCATTCA ACAAGCACCT AGTAAGTGCC TGCTGTATCC
3151  CTACATTACA CAGTTCAGCC TTTATCAAGC TTAGTGAGCA GTGAGCACTG
3201  AAACATTATT TTTTAATGTT TAAAAAGTTT CTAATATTAA AGTCAGAATA
3251  TTAATACAAT TAATATTAAT ATTAACTACA GAAAAGACAA ACAGTAGAGA
3301  ACAGCAAAAA AATAAAAAGG ATCTCCTTTT TTCCCAGCCC AAATTCTCCT
3351  CTCTAAAAGT GTCCACAAGA AGGGGTGTTT ATTCTTCCAA CACATTTCAC
3401  TTTTCTGTAA ATATACATAA ACTTAAAAAG AAAACCTCAT GGAGTCATCT
3451  TGCACACACT TTTCATGCAG TGCTCTTTGT AGCTAAACAG TGAAGATTTA
3501  CCTCGTTCTG CTCAGAGGCC TTGCTGTGGA GCTCCACTGC CATGTACCCA
3551  GTAGGGTTTG ACATTTCATT AGCCATGCAA CATGGATATG TATTGGGCAG
3601  CAGACTGTGT TTCGTGAACT GCAGTGATGT ATACATCTTA TAGATGCAAA
3651  GTATTTTGGG GTATATTATC CTAAGGGAAG ATAAAGATGA TATTAAGAAC
3701  TGCTGTTTCA CGGGGCCCTT ACCTGTGACC CTCTTTGCTG AAGAATATTT
3751  AACCCCACAC AGCACTTCAA AGAAGCTGTC TTGGAAGTCT GTCTCAGGAG
3801  CACCCTGTCT TCTTAATTCT CCAAGCGGAT GCTCCATTTC AATTGCTTTG
3851  TGACTTCTTC TTCTTTGTTT TTTTAAATAT TATGCTGCTT TAACAGTGGA
3901  GCTGAATTTT CTGGAAAATG CTTCTTGGCT GGGGCCACTA CCTCCTTTCC
3951  TATCTTTACA TCTATGTGTA TGTTGACTTT TTAAAATTCT GAGTGATCCA
4001  GGGTATGACC TAGGGAATGA ACTAGCTATG GAAATAACTC AGGGTTAGGA
4051  ATCCTAGCAC TTGTCTCAGG ACTCTGAAAA GGAACGGCTT CCTCATTCCT
4101  TGTCTTGATA AAGTGGAATT GGCAAACTAG AATTTAGTTT GTACTCAGTG
4151  GACAGTGCTG TTGAAGATTT GAGGACTTGT TAAAGAGCAC TGGGTCATAT
4201  GGAAAAAATG TATGTGTCTC CCCAGGTGCA TTTTCTTGGT TTATGTCTTG
4251  TTCTTGAGAT TTTGTATATT TAGGAAAACC TCAAGCAGTA ATTAATATCT
4301  CCTGGAACAC TATAGAGAAC CAAGTGACCG ACTCATTTAC AACTGAAACC
4351  TAGGAAGCCC CTGAGTCCTG AGCGAAAACA GGAGAGTTAG TCGCCCTACA
4401  GAAAACCCAG CTAGACTATT GGGTATGAAC TAAAAGAGA CTGTGCCATG
4451  GTGAGAAAAA TGTAAAATCC TACAGTGGAA TGAGCAGCCC TTACAGTGTT
4501  GTTACCACCA AGGGCAGGTA GGTATTAGTG TTTGAAAAAG CTGGTCTTTG
4551  AGCGAGGGCA TAAATACAGC TAGCCCCAGG GGTGGAACAA CTGTGGGAGT
4601  CTTGGGTACT CGCACCTCTT GGCTTTGTTG ATGCTCCGCC AGGAAGGCCA
4651  CTTGTGTGTG CGTGTCAGTT ACTTTTTTAG TAACAATTCA GATCCAGTGT
4701  AAACTTCCGT TCATTGCTCT CCAGTCACAT GCCCCACTT CCCCACAGGT
4751  GAAAGTTTTT CTGAAGTGTT GGGATTGGTT AAGGTCTTTA TTTGTATTAC
4801  GTATCTCCCC AAGTCCTCTG TGGCCAGCTG CATCTGTCTG AATGGTGCGT
4851  GAAGGCTCTC AGACCTTACA CACCATTTTG TAAGTTATGT TTTACATGCC
4901  CCGTTTTGA GACTGATCTC GATGCAGGTG GATCTCCTTG AGATCCTGAT
4951  AGCCTGTTAC AGGAATGAAG TAAAGGTCAG TTTTTTTTGT ATTGATTTTC
5001  ACAGCTTTGA GGAACATGCA TAAGAAATGT AGCTGAAGTA GAGGGGACGT
5051  GAGAGAAGGG CCAGGCCGGC AGGCCAACCC TCCTCCAATG GAAATTCCCG
5101  TGTTGCTTCA AACTGAGACA GATGGGACTT AACAGGCAAT GGGGTCCACT
5151  TCCCCCTCTT CAGCATCCCC CGTACC
```

FIG. 6A

| | | | | |
|---|---|---|---|---|
| Hum MUM-1 (23-72) | KLRQWLIDQI | DSGKYPGLIW | ENEEKSIFRI | PWKHAGKQDY | NREEDAALFK |
| Mus LSIRF (23-72) | KLRQWLIDQI | DSGKYPGLIW | ENEEKSVFRI | PWKHAGKQDY | NREEDAALFK |
| Hum IRF-1 (7-56) | RMRPWLEMQI | NSNQIPGLIW | INKEEMIFQI | PWKHAAKHGW | DINKDACLFR |
| Hum IRF-2 (7-56) | RMRPWLEEQI | NSNTIPGLKW | LNKEKIFQI | PWMHAARHGW | DVEKDAPLFR |
| Hum ICSBP (9-60) | RLRQWLIEQI | DSSMYPGLIW | ENEEKSMFRI | PWKHAGKQDY | NQEVDASIFK |
| Hum ISGF3γ (11-60) | KLRNWVEQV | ESGQFPGVCW | DDTAKTMFRI | PWKHAGKQDF | REDQDAAFFK |
| Hum IRF-3 (7-55) | RILPWLVSQL | DLGQLEGVAW | VNKSRTRFRI | PWKHGLRQD. | AQQEDFGIEQ |

| | | | | |
|---|---|---|---|---|
| Hum MUM-1 (73-122) | AWALFKGKFR | EGIDKPDPPT | WKTRLRCALN | KSNDFEELVE | RSQLDISDPY |
| Mus LSIRF (73-122) | AWALFKGKFR | EGIDKPDPPT | WKTRLRCALN | KSNDFEELVE | RSQLDISDPY |
| Hum IRF-1 (57-106) | SWAIHTGRYK | AGEKEPDPKT | WKANFRCAMN | SLPDIEEVKD | QSRNKGSSAV |
| Hum IRF-2 (57-106) | NWAIHTGKHQ | PGVDKPDPKT | WKANFRCAMN | SLPDIEEVKD | KSIKKGNNAF |
| Hum ICSBP (59-107) | AWAVFKGKFK | EG.DKAEPAT | WKTRLRCALN | KSPDFEEVTD | RSQLDISEPY |
| Hum ISGF3γ (61-109) | AWAIFKGKYK | EG.DTGGPAV | WKTRLRCALN | KSSEFKEVPE | RGRMDVAEPY |
| Hum IRF-3 (56-104) | AWAEATGAYV | PGRDKPDLPT | WKRNFRSALN | RKEGLRLAED | RSK..DPHDPH |

| | |
|---|---|
| Hum MUM-1 (123-130) | KVYRIVPE |
| Mus LSIRF (123-130) | KVYRIVPE |
| Hum IRF-1 (107-114) | RVYRMLPP |
| Hum IRF-2 (107-114) | RVYRMLPL |
| Hum ICSBP (108-115) | KVYRIVPE |
| Hum ISGF3γ (110-117) | KVYQLIPP |
| Hum IRF-3 (105-112) | KIYEFVNS |

FIG. 6B

```
Hum MUM-1  (327-372)  KRLCQSTIYW  DGPLAL.....  CNDRPNKLER  DQTCKLEDTQ  QFLSELQAFA
Mus LSIRF  (327-372)  KRLCQSRIYW  DGPLAL.....  CSDRPNKLER  DQTCKLEDTQ  QFLSELQVEA
Hum ICSBP  (289-334)  KRLCQGRVFC  SGNAVV.....  CKGRPNKLER  DEVVQVEDTS  QFRELQQEY
Hum ISGF3γ (290-335)  QRLCPIPISW  NAPQAP.....  PGPGPHLLPS  NECVELERTA  YECRDLVRYF
Hum IRF-3  (284-333)  QRLGHCHTYW  AVSEELLPNS  GHGPDGEVPK  DKEGGVEDLG  PFIVDLITET

Hum MUM-1  (373-421)  HHGRSLPRFQ  VTLCFGEEFP  DPQRQR.KLI  TAHVEPLLAR  QLYYFAQQNS
Mus LSIRF  (373-421)  HHGRPAPRFQ  VTLCFGEEFP  DPQRQR.KLI  TAHVEPLLAR  QLYYFAQQNT
Hum ICSBP  (335-384)  NSQGRLPDGR  VLCFGEEFP  DMAPLRSKLI  LVQIEQLYVR  QLAEEAGKSC
Hum ISGF3γ (336-385)  QGLGPPPKFQ  VTLNFWEESH  GSSHTPQNLI  TVKMEQAFAR  YLEQTPEQQ
Hum IRF-3  (334-383)  EGSGRSPRYA  LWFCVGESWP  QDQPWTKRLV  MVKVVPTCLR  ALVEMARVGG
```

MUM1 AND IgH TRANSLOCATION SCHEME
VH-D-J-CH indicates variable-diversity joining-constant region B, *Bam*HI; H, *Hin*dIII; S, *Sac*II; X, *Xba*I; Xh, *Xho*I ↓ chromosomal breakpoint pMUM2-8 has a 22.0kb insert in BamHI site of pBluescript KS+.

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 108 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Lys Leu Arg Gln Trp Leu Ile Asp Gln Ile Asp Ser Gly Lys Tyr Pro
1               5                   10                  15

Gly Leu Val Trp Glu Asn Glu Glu Lys Ser Ile Phe Arg Ile Pro Trp
            20                  25                  30

Lys His Ala Gly Lys Gln Asp Tyr Asn Arg Glu Glu Asp Ala Ala Leu
        35                  40                  45

Phe Lys Ala Trp Ala Leu Phe Lys Gly Lys Phe Arg Glu Gly Ile Asp
    50                  55                  60

Lys Pro Asp Pro Thr Trp Lys Thr Arg Leu Arg Cys Ala Leu Asn
65                  70                  75                  80

Lys Ser Asn Asp Phe Glu Glu Leu Val Glu Arg Ser Gln Leu Asp Ile
            85                  90                  95

Ser Asp Pro Tyr Lys Val Tyr Arg Ile Val Pro Glu
            100                 105
```

(2) INFORMATION FOR SEQ ID NO:2:

(i) SEQUENCE CHARACTERISTICS:
      (A) LENGTH: 108 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

```
Lys Leu Arg Gln Trp Leu Ile Asp Gln Ile Asp Ser Gly Lys Tyr Pro
1               5                   10                  15

Gly Leu Val Trp Glu Asn Glu Glu Lys Ser Val Phe Arg Ile Pro Trp
            20                  25                  30
```

```
Lys His Ala Gly Lys Gln Asp Tyr Asn Arg Glu Glu Asp Ala Ala Leu
        35                  40                  45

Phe Lys Ala Trp Ala Leu Phe Lys Gly Lys Phe Arg Glu Gly Ile Asp
        50                  55                  60

Lys Pro Asp Pro Thr Trp Lys Thr Arg Leu Arg Cys Ala Leu Asn
 65                  70                  75                  80

Lys Ser Asn Asp Phe Glu Glu Leu Val Glu Arg Ser Gln Leu Asp Ile
                85                  90                  95

Ser Asp Pro Tyr Lys Val Tyr Arg Ile Val Pro Glu
                100                 105
```

(2) INFORMATION FOR SEQ ID NO:3:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Arg Met Arg Pro Trp Leu Glu Met Gln Ile Asn Ser Asn Gln Ile Pro
 1                   5                  10                  15

Gly Leu Ile Trp Ile Asn Lys Glu Glu Met Ile Phe Gln Ile Pro Trp
                20                  25                  30

Lys His Ala Ala Lys His Gly Trp Asp Ile Asn Lys Asp Ala Cys Leu
        35                  40                  45

Phe Arg Ser Trp Ala Ile His Thr Gly Arg Tyr Lys Ala Gly Glu Lys
        50                  55                  60

Glu Pro Asp Pro Lys Thr Trp Lys Ala Asn Phe Arg Cys Ala Met Asn
 65                  70                  75                  80

Ser Leu Pro Asp Ile Glu Glu Val Lys Asp Gln Ser Arg Asn Lys Gly
                85                  90                  95

Ser Ser Ala Val Arg Val Tyr Arg Met Leu Pro Pro
                100                 105
```

(2) INFORMATION FOR SEQ ID NO:4:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Arg Met Arg Pro Trp Leu Glu Glu Gln Ile Asn Ser Asn Thr Ile Pro
 1                   5                  10                  15

Gly Leu Lys Trp Leu Asn Lys Glu Lys Lys Ile Phe Gln Ile Pro Trp
                20                  25                  30

Met His Ala Ala Arg His Gly Trp Asp Val Glu Lys Asp Ala Pro Leu
        35                  40                  45

Phe Arg Asn Trp Ala Ile His Thr Gly Lys His Gln Pro Gly Val Asp
        50                  55                  60

Lys Pro Asp Pro Lys Thr Trp Lys Ala Asn Phe Arg Cys Ala Met Asn
 65                  70                  75                  80

Ser Leu Pro Asp Ile Glu Glu Val Lys Asp Lys Ser Ile Lys Lys Gly
```

```
                           85                  90                  95

Asn Asn Ala Phe Arg Val Tyr Arg Met Leu Pro Leu
                100                 105

(2) INFORMATION FOR SEQ ID NO:5:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Arg Leu Arg Gln Trp Leu Ile Glu Gln Ile Asp Ser Ser Met Tyr Pro
1               5                   10                  15

Gly Leu Ile Trp Glu Asn Glu Glu Lys Ser Met Phe Arg Ile Pro Trp
                20                  25                  30

Lys His Ala Gly Lys Gln Asp Tyr Asn Gln Glu Val Asp Ala Ser Ile
            35                  40                  45

Phe Lys Ala Trp Ala Val Phe Lys Gly Lys Phe Lys Glu Gly Asp Lys
50                  55                  60

Ala Glu Pro Ala Thr Trp Lys Thr Arg Leu Arg Cys Ala Leu Asn Lys
65                  70                  75                  80

Ser Pro Asp Phe Glu Glu Val Thr Asp Arg Ser Gln Leu Asp Ile Ser
                85                  90                  95

Glu Pro Tyr Lys Val Tyr Arg Ile Val Pro Glu
                100                 105

(2) INFORMATION FOR SEQ ID NO:6:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Lys Leu Arg Asn Trp Val Val Glu Gln Val Glu Ser Gly Gln Phe Pro
1               5                   10                  15

Gly Val Cys Trp Asp Asp Thr Ala Lys Thr Met Phe Arg Ile Pro Trp
                20                  25                  30

Lys His Ala Gly Lys Gln Asp Phe Arg Glu Asp Gln Asp Ala Ala Phe
            35                  40                  45

Phe Lys Ala Trp Ala Ile Phe Lys Gly Lys Tyr Lys Glu Gly Asp Thr
50                  55                  60

Gly Gly Pro Ala Val Trp Lys Thr Arg Leu Arg Cys Ala Leu Asn Lys
65                  70                  75                  80

Ser Ser Glu Phe Lys Glu Val Pro Glu Arg Gly Arg Met Asp Val Ala
                85                  90                  95

Glu Pro Tyr Lys Val Tyr Gln Leu Leu Pro Pro
                100                 105

(2) INFORMATION FOR SEQ ID NO:7:

(i) SEQUENCE CHARACTERISTICS:
        (A) LENGTH: 106 amino acids
        (B) TYPE: amino acid
```

(C) STRANDEDNESS: single
(D) TOPOLOGY: linear (ii) MOLECULE TYPE: peptide (xi) SEQUENCE DESCRIPTION: SEQ ID NO:7:

Arg Ile Leu Pro Trp Leu Val Ser Gln Leu Asp Leu Gly Gln Leu Glu
 1               5                  10                  15

Gly Val Ala Trp Val Asn Lys Ser Arg Thr Arg Phe Arg Ile Pro Trp
                20                  25                  30

Lys His Gly Leu Arg Gln Asp Ala Gln Gln Glu Asp Phe Gly Ile Phe
                35                  40                  45

Gln Ala Trp Ala Glu Ala Thr Gly Ala Tyr Val Pro Gly Arg Asp Lys
        50                  55                  60

Pro Asp Leu Pro Thr Trp Lys Arg Asn Phe Arg Ser Ala Leu Asn Arg
65                  70                  75                  80

Lys Glu Gly Leu Arg Leu Ala Glu Asp Arg Ser Lys Asp Pro His Asp
                85                  90                  95

Pro His Lys Ile Tyr Glu Phe Val Asn Ser
                100                 105

(2) INFORMATION FOR SEQ ID NO:8:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Lys Arg Leu Cys Gln Ser Thr Ile Tyr Trp Asp Gly Pro Leu Ala Leu
 1               5                  10                  15

Cys Asn Asp Arg Pro Asn Lys Leu Glu Arg Asp Gln Thr Cys Lys Leu
                20                  25                  30

Phe Asp Thr Gln Gln Phe Leu Ser Glu Leu Gln Ala Phe Ala His His
                35                  40                  45

Gly Arg Ser Leu Pro Arg Phe Gln Val Thr Leu Cys Phe Gly Glu Glu
        50                  55                  60

Phe Pro Asp Pro Gln Arg Gln Arg Lys Leu Ile Thr Ala His Val Glu
65                  70                  75                  80

Pro Leu Leu Ala Arg Gln Leu Tyr Tyr Phe Ala Gln Gln Asn Ser
                85                  90                  95

(2) INFORMATION FOR SEQ ID NO:9:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Lys Arg Leu Cys Gln Ser Arg Ile Tyr Trp Asp Gly Pro Leu Ala Leu
 1               5                  10                  15

Cys Ser Asp Arg Pro Asn Lys Leu Glu Arg Asp Gln Thr Cys Lys Leu
                20                  25                  30

Phe Asp Thr Gln Gln Phe Leu Ser Glu Leu Gln Val Phe Ala His His

```
                35                  40                  45
Gly Arg Pro Ala Pro Arg Phe Gln Val Thr Leu Cys Phe Gly Glu Glu
            50                  55                  60

Phe Pro Asp Pro Gln Arg Gln Arg Lys Leu Ile Thr Ala His Val Glu
65                  70                  75                  80

Pro Leu Leu Ala Arg Gln Leu Tyr Tyr Phe Ala Gln Gln Asn Thr
                85                  90                  95
```

(2) INFORMATION FOR SEQ ID NO:10:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Lys Arg Leu Cys Gln Gly Arg Val Phe Cys Ser Gly Asn Ala Val Val
1               5                  10                  15

Cys Lys Gly Arg Pro Asn Lys Leu Glu Arg Asp Glu Val Val Gln Val
            20                  25                  30

Phe Asp Thr Ser Gln Phe Arg Glu Leu Gln Gln Phe Tyr Asn Ser
                35                  40                  45

Gln Gly Arg Leu Pro Asp Gly Arg Val Val Leu Cys Phe Gly Glu Glu
            50                  55                  60

Phe Pro Asp Met Ala Pro Leu Arg Ser Lys Leu Ile Leu Val Gln Ile
65                  70                  75                  80

Glu Gln Leu Tyr Val Arg Gln Leu Ala Glu Glu Ala Gly Lys Ser Cys
                85                  90                  95
```

(2) INFORMATION FOR SEQ ID NO:11:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Gln Arg Leu Cys Pro Ile Pro Ile Ser Trp Asn Ala Pro Gln Ala Pro
1               5                  10                  15

Pro Gly Pro Gly Pro His Leu Leu Pro Ser Asn Glu Cys Val Glu Leu
            20                  25                  30

Phe Arg Thr Ala Tyr Phe Cys Arg Asp Leu Val Arg Tyr Phe Gln Gly
                35                  40                  45

Leu Gly Pro Pro Pro Lys Phe Gln Val Thr Leu Asn Phe Trp Glu Glu
            50                  55                  60

Ser His Gly Ser Ser His Thr Pro Gln Asn Leu Ile Thr Val Lys Met
65                  70                  75                  80

Glu Gln Ala Phe Ala Arg Tyr Leu Leu Glu Gln Thr Pro Glu Gln Gln
                85                  90                  95
```

(2) INFORMATION FOR SEQ ID NO:12:

(i) SEQUENCE CHARACTERISTICS:
        (A) LENGTH: 100 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO:12:

Gln Arg Leu Gly His Cys His Thr Tyr Trp Ala Val Ser Glu Glu Leu
1               5                  10                 15

Leu Pro Asn Ser Gly His Gly Pro Asp Gly Glu Val Pro Lys Asp Lys
                20                  25                  30

Glu Gly Gly Val Phe Asp Leu Gly Pro Phe Ile Val Asp Leu Ile Thr
            35                  40                  45

Phe Thr Glu Gly Ser Gly Arg Ser Pro Arg Tyr Ala Leu Trp Phe Cys
        50                  55                  60

Val Gly Glu Ser Trp Pro Gln Asp Gln Pro Trp Thr Lys Arg Leu Val
65                  70                  75                  80

Met Val Lys Val Val Pro Thr Cys Leu Arg Ala Leu Val Glu Met Ala
                85                  90                  95

Arg Val Gly Gly
            100

(2) INFORMATION FOR SEQ ID NO:13:

(i) SEQUENCE CHARACTERISTICS:
        (A) LENGTH: 5176 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 217..1569

(xi) SEQUENCE DESCRIPTION: SEQ ID NO:13:

GCCTGACCAA CATGGTAAAA CCCCATCTCT GCTAAAACTA CAAAAAATTA GCTGGATGTG        60

GTGGCAGGGA ACCTGTCATC CCAGCTAGTT GGGAGACTGA GGCAGGAGAA TCGCTCGATC       120

TTGGGACCCA CCGCTGCCCT CAGCTCCGAG TCCAGGGCGA GTGCAGAGCA CAGCGGGCGG       180

AGGACCCCGG GCGCGGGCGC GGACGGCACG CGGGGC ATG AAC CTG GAG GGC GGC        234
                                        Met Asn Leu Glu Gly Gly
                                        1               5

GGC CGA GGC GGA GAG TTC GGC ATG AGC GCG GTG AGC TGC GGC AAC GGG        282
Gly Arg Gly Gly Glu Phe Gly Met Ser Ala Val Ser Cys Gly Asn Gly
            10                  15                  20

AAG CTC CGC CAG TGG CTG ATC GAC CAG ATC GAC AGC GGC AAG TAC CCC        330
Lys Leu Arg Gln Trp Leu Ile Asp Gln Ile Asp Ser Gly Lys Tyr Pro
            25                  30                  35

GGG CTG GTG TGG GAG AAC GAG GAG AAG AGC ATC TTC CGC ATC CCC TGG        378
Gly Leu Val Trp Glu Asn Glu Glu Lys Ser Ile Phe Arg Ile Pro Trp
        40                  45                  50

AAG CAC GCG GGC AAG CAG GAC TAC AAC CGC GAG GAG GAC GCC GCG CTC        426
Lys His Ala Gly Lys Gln Asp Tyr Asn Arg Glu Glu Asp Ala Ala Leu
55                  60                  65                  70

TTC AAG GCT TGG GCA CTG TTT AAA GGA AAG TTC CGA GAA GGC ATC GAC        474
Phe Lys Ala Trp Ala Leu Phe Lys Gly Lys Phe Arg Glu Gly Ile Asp
            75                  80                  85

AAG CCG GAC CCT CCC ACC TGG AAG ACG CGC CTG CGG TGC GCT TTG AAC        522
Lys Pro Asp Pro Pro Thr Trp Lys Thr Arg Leu Arg Cys Ala Leu Asn
            90                  95                  100
```

-continued

| | |
|---|---|
| AAG AGC AAT GAC TTT GAG GAA CTG GTT GAG CGG AGC CAG CTG GAC ATC<br>Lys Ser Asn Asp Phe Glu Glu Leu Val Glu Arg Ser Gln Leu Asp Ile<br>105                    110                    115 | 570 |
| TCA GAC CCG TAC AAA GTG TAC AGG ATT GTT CCT GAG GGA GCC AAA AAA<br>Ser Asp Pro Tyr Lys Val Tyr Arg Ile Val Pro Glu Gly Ala Lys Lys<br>120                    125                    130 | 618 |
| GGA GCC AAG CAG CTC ACC CTG GAG GAC CCG CAG ATG TCC ATG AGC CAC<br>Gly Ala Lys Gln Leu Thr Leu Glu Asp Pro Gln Met Ser Met Ser His<br>135                    140                    145                    150 | 666 |
| CCC TAC ACC ATG ACA ACG CCT TAC CCT TCG CTC CCA GCC CAG CAG GTT<br>Pro Tyr Thr Met Thr Thr Pro Tyr Pro Ser Leu Pro Ala Gln Gln Val<br>                    155                    160                    165 | 714 |
| CAC AAC TAC ATG ATG CCA CCC CTC GAC CGA AGC TGG AGG GAC TAC GTC<br>His Asn Tyr Met Met Pro Pro Leu Asp Arg Ser Trp Arg Asp Tyr Val<br>                    170                    175                    180 | 762 |
| CCG GAT CAG CCA CAC CCG GAA ATC CCG TAC CAA TGT CCC ATG ACG TTT<br>Pro Asp Gln Pro His Pro Glu Ile Pro Tyr Gln Cys Pro Met Thr Phe<br>185                    190                    195 | 810 |
| GGA CCC CGC GGC CAC CAC TGG CAA GGC CCA GCT TGT GAA AAT GGT TGC<br>Gly Pro Arg Gly His His Trp Gln Gly Pro Ala Cys Glu Asn Gly Cys<br>200                    205                    210 | 858 |
| CAG GTG ACA GGA ACC TTT TAT GCT TGT GCC CCA CCT GAG TCC CAG GCT<br>Gln Val Thr Gly Thr Phe Tyr Ala Cys Ala Pro Pro Glu Ser Gln Ala<br>215                    220                    225                    230 | 906 |
| CCC GGA GTC CCC ACA GAG CCA AGC ATA AGG TCT GCC GAA GCC TTG GCG<br>Pro Gly Val Pro Thr Glu Pro Ser Ile Arg Ser Ala Glu Ala Leu Ala<br>                    235                    240                    245 | 954 |
| TTC TCA GAC TGC CGG CTG CAC ATC TGC CTG TAC TAC CGG GAA ATC CTC<br>Phe Ser Asp Cys Arg Leu His Ile Cys Leu Tyr Tyr Arg Glu Ile Leu<br>                    250                    255                    260 | 1002 |
| GTG AAG GAG CTG ACC ACG TCC AGC CCC GAG GGC TGC CGG ATC TCC CAT<br>Val Lys Glu Leu Thr Thr Ser Ser Pro Glu Gly Cys Arg Ile Ser His<br>265                    270                    275 | 1050 |
| GGA CAT ACG TAT GAC GCC AGC AAC CTG GAC CAG GTC CTG TTC CCC TAC<br>Gly His Thr Tyr Asp Ala Ser Asn Leu Asp Gln Val Leu Phe Pro Tyr<br>280                    285                    290 | 1098 |
| CCA GAG GAC AAT GGC CAC AGG AAA AAC ATT GAG AAC CTG CTG AGC CAC<br>Pro Glu Asp Asn Gly His Arg Lys Asn Ile Glu Asn Leu Leu Ser His<br>295                    300                    305                    310 | 1146 |
| CTG GAG AGG GGC GTG GTC CTC TGG ATG GCC CCC GAC GGG CTC TAT GCG<br>Leu Glu Arg Gly Val Val Leu Trp Met Ala Pro Asp Gly Leu Tyr Ala<br>                    315                    320                    325 | 1194 |
| AAA AGA CTG TGC CAG AGC ACG ATC TAC TGG GAC GGG CCC CTG GCG CTG<br>Lys Arg Leu Cys Gln Ser Thr Ile Tyr Trp Asp Gly Pro Leu Ala Leu<br>                    330                    335                    340 | 1242 |
| TGC AAC GAC CGG CCC AAC AAA CTG GAG AGA GAC CAG ACC TGC AAG CTC<br>Cys Asn Asp Arg Pro Asn Lys Leu Glu Arg Asp Gln Thr Cys Lys Leu<br>                    345                    350                    355 | 1290 |
| TTT GAC ACA CAG CAG TTC TTG TCA GAG CTG CAA GCG TTT GCT CAC CAC<br>Phe Asp Thr Gln Gln Phe Leu Ser Glu Leu Gln Ala Phe Ala His His<br>                    360                    365                    370 | 1338 |
| GGC CGC TCC CTG CCA AGA TTC CAG GTG ACT CTA TGC TTT GGA GAG GAG<br>Gly Arg Ser Leu Pro Arg Phe Gln Val Thr Leu Cys Phe Gly Glu Glu<br>375                    380                    385                    390 | 1386 |
| TTT CCA GAC CCT CAG AGG CAA AGA AAG CTC ATC ACA GCT CAC GTA GAA<br>Phe Pro Asp Pro Gln Arg Gln Arg Lys Leu Ile Thr Ala His Val Glu<br>                    395                    400                    405 | 1434 |
| CCT CTG CTA GCC AGA CAA CTA TAT TAT TTT GCT CAA CAA AAC AGT GGA<br>Pro Leu Leu Ala Arg Gln Leu Tyr Tyr Phe Ala Gln Gln Asn Ser Gly<br>                    410                    415                    420 | 1482 |

```
CAT TTC CTG AGG GGC TAC GAT TTA CCA GAA CAC ATC AGC AAT CCA GAA         1530
His Phe Leu Arg Gly Tyr Asp Leu Pro Glu His Ile Ser Asn Pro Glu
            425                 430                 435

GAT TAC CAC AGA TCT ATC CGC CAT TCC TCT ATT CAA GAA TGAAAAATGT          1579
Asp Tyr His Arg Ser Ile Arg His Ser Ser Ile Gln Glu
        440                 445                 450

CAAGATGAGT GGTTTTCTTT TTCCTTTTTT TTTTTTTTTT TTTTGATACG GAGATACGGG       1639

GTCTTGCTCT GTCTCCCAGG CTGGAGTGCA GTGACACAAT CTCAGCTCAC TGTGACCTCC       1699

GCCTCCTGGG TTCAAGAGAC TCTCCTGCCT CAGCCTCCCT GGTAGCTGGG ATTACAGGTG       1759

TGAGCCACTG CACCCACCCA AGACAAGTGA TTTTCATTGT AAATATTTGA CTTTAGTGAA       1819

AGCGTCCAAT TGACTGCCCT CTTACTGTTT TGAGGAACTC AGAAGTGGAG ATTTCAGTTC       1879

AGCGGTTGAG GAGAATTGCG GCGAGACAAG CATGGAAAAT CAGTGACATC TGATTGGCAG       1939

ATGAGCTTAT TTCAAAAGGA AGGGTGGCTT TGCATTTTCT TGTGTTCTGT AGACTGCCAT       1999

CATTGATGAT CACTGTGAAA ATTGACCAAG TGATGTGTTT ACATTTACTG AAATGCGCTC       2059

TTTAATTTGT TGTAGATTAG GTCTTGCTGG AAGACAGAGA AAACTTGCCT TCAGTATTG        2119

ACACTGACTA GAGTGATGAC TGCTTGTAGG TATGTCTGTG CCATTTCTCA GGGAAGTAAG      2179

ATGTAAATTG AAGAAGCCTC ACACGTAAAA GAAATGTATT AATGTATGTA GGAGCTGCAG      2239

TTCTTGTGGA AGACACTTGC TGAGTGAAGG AAATGAATCT TTGACTGAAG CCGTGCCTGT      2299

AGCCTTGGGG AGGCCCATCC CCCACCTGCC AGCGGTTTCC TGGTGTGGGT CCCTCTGCCC      2359

CACCCTCCTT CCCATTGGCT TTCTCTCCTT GGCCTTTCCT GGAAGCCAGT TAGTAAACTT      2419

CCTATTTTCT TGAGTCAAAA AACATGAGCG CTACTCTTGG ATGGGACATT TTTGTCTGTC      2479

CTACAATCTA GTAATGTCTA AGTAATGGTT AAGTTTTCTT GTTTCTGCAT CTTTTTGACC      2539

CTCATTCTTT AGAGATGCTA AAATTCTTCG CATAAAGAAG AAGAAATTAA GGAACATAAA      2599

TCTTAATACT TGAACTGTTG CCCTTCTGTC CAAGTACTTA ACTATCTGTT CCCTTCCTCT      2659

GTGCCACGCT CCTCTGTTTG TTTGGCTGTC CAGCGATCAG CCATGGCGAC ACTAAAGGAG      2719

GAGGAGCCGG GGACTCCCAG GCTGGAGAGC ACTGCCAGGA CCCACCACTG GAAGCAGGAT      2779

GGAGCTGACT ACGGAACTGC ACACTCAGTG GGCTGTTTCT GCTTATTTCA TCTGTTCTAT      2839

GCTTCCTCGT GCCAATTATA GTTTGACAGG GCCTTAAAAT TACTTGGCTT TTTCCAAATG      2899

CTTCTATTTA TAGAAATCCC AAAGACCTCC ACTTGCTTAA GTATACCTAT CACTTACATT      2959

TTTGTGGTTT TGAGAAAGTA CAGCAGTAGA CTGGGGCGTC ACCTCCAGGC CGTTTCTCAT      3019

ACTACAGGAT ATTTACTATT ACTCCCAGGA TTCAGCAGAA GATTGCGTTA GCTCTCAAAT      3079

GTGTGTTCCT GCTTTTCTAA TGGATATTTT AAATTCATTC AACAAGCACC TAGTAAGTGC      3139

CTGCTGTATC CCTACATTAC ACAGTTCAGC CTTTATCAAG CTTAGTGAGC AGTGAGCACT      3199

GAAACATTAT TTTTTAATGT TTAAAAAGTT TCTAATATTA AAGTCAGAAT ATTAATACAA      3259

TTAATATTAA TATTAACTAC AGAAAAGACA AACAGTAGAG AACAGCAAAA AAATAAAAAG      3319

GATCTCCTTT TTTCCCAGCC CAAATTCTCC TCTCTAAAAG TGTCCACAAG AAGGGGTGTT      3379

TATTCTTCCA ACACATTTCA CTTTTCTGTA AATATACATA AACTTAAAAA GAAAACCTCA      3439

TGGAGTCATC TTGCACACAC TTTTCATGCA GTGCTCTTTG TAGCTAAACA GTGAAGATTT      3499

ACCTCGTTCT GCTCAGAGGC CTTGCTGTGG AGCTCCACTG CCATGTACCC AGTAGGGTTT      3559

GACATTTCAT TAGCCATGCA ACATGGATAT GTATTGGGCA GCAGACTGTG TTTCGTGAAC      3619

TGCAGTGATG TATACATCTT ATAGATGCAA AGTATTTTGG GGTATATTAT CCTAAGGGAA      3679
```

-continued

```
GATAAAGATG ATATTAAGAA CTGCTGTTTC ACGGGGCCCT TACCTGTGAC CCTCTTTGCT    3739

GAAGAATATT TAACCCCACA CAGCACTTCA AAGAAGCTGT CTTGGAAGTC TGTCTCAGGA    3799

GCACCCTGTC TTCTTAATTC TCCAAGCGGA TGCTCCATTT CAATTGCTTT GTGACTTCTT    3859

CTTCTTTGTT TTTTTAAATA TTATGCTGCT TTAACAGTGG AGCTGAATTT CTGGAAAAT    3919

GCTTCTTGGC TGGGGCCACT ACCTCCTTTC CTATCTTTAC ATCTATGTGT ATGTTGACTT    3979

TTTAAAATTC TGAGTGATCC AGGGTATGAC CTAGGGAATG AACTAGCTAT GGAAATAACT    4039

CAGGGTTAGG AATCCTAGCA CTTGTCTCAG GACTCTGAAA AGGAACGGCT TCCTCATTCC    4099

TTGTCTTGAT AAAGTGGAAT TGGCAAACTA GAATTTAGTT TGTACTCAGT GGACAGTGCT    4159

GTTGAAGATT TGAGGACTTG TTAAAGAGCA CTGGGTCATA TGGAAAAAAT GTATGTGTCT    4219

CCCCAGGTGC ATTTTCTTGG TTTATGTCTT GTTCTTGAGA TTTTGTATAT TTAGGAAAAC    4279

CTCAAGCAGT AATTAATATC TCCTGGAACA CTATAGAGAA CCAAGTGACC GACTCATTTA    4339

CAACTGAAAC CTAGGAAGCC CCTGAGTCCT GAGCGAAAAC AGGAGAGTTA GTCGCCCTAC    4399

AGAAAACCCA GCTAGACTAT TGGGTATGAA CTAAAAAGAG ACTGTGCCAT GGTGAGAAAA    4459

ATGTAAAATC CTACAGTGGA ATGAGCAGCC CTTACAGTGT TGTTACCACC AAGGGCAGGT    4519

AGGTATTAGT GTTTGAAAAA GCTGGTCTTT GAGCGAGGGC ATAAATACAG CTAGCCCCAG    4579

GGGTGGAACA ACTGTGGGAG TCTTGGGTAC TCGCACCTCT TGGCTTTGTT GATGCTCCGC    4639

CAGGAAGGCC ACTTGTGTGT GCGTGTCAGT TACTTTTTTA GTAACAATTC AGATCCAGTG    4699

TAAACTTCCG TTCATTGCTC TCCAGTCACA TGCCCCCACT TCCCCACAGG TGAAAGTTTT    4759

TCTGAAGTGT TGGGATTGGT TAAGGTCTTT ATTTGTATTA CGTATCTCCC CAAGTCCTCT    4819

GTGGCCAGCT GCATCTGTCT GAATGGTGCG TGAAGGCTCT CAGACCTTAC ACACCATTTT    4879

GTAAGTTATG TTTTACATGC CCCGTTTTTG AGACTGATCT CGATGCAGGT GGATCTCCTT    4939

GAGATCCTGA TAGCCTGTTA CAGGAATGAA GTAAAGGTCA GTTTTTTTG TATTGATTTT    4999

CACAGCTTTG AGGAACATGC ATAAGAAATG TAGCTGAAGT AGAGGGGACG TGAGAGAAGG    5059

GCCAGGCCGG CAGGCCAACC CTCCTCCAAT GGAAATTCCC GTGTTGCTTC AAACTGAGAC    5119

AGATGGGACT TAACAGGCAA TGGGGTCCAC TTCCCCCTCT TCAGCATCCC CCGTACC       5176
```

(2) INFORMATION FOR SEQ ID NO:14:

(i) SEQUENCE CHARACTERISTICS:
        (A) LENGTH: 451 amino acids
        (B) TYPE: amino acid
        (D) TOPOLOGY: linear (ii) MOLECULE TYPE: protein (xi) SEQUENCE DESCRIPTION: SEQ ID NO:14:

```
Met Asn Leu Glu Gly Gly Gly Arg Gly Gly Glu Phe Gly Met Ser Ala
 1               5                  10                  15

Val Ser Cys Gly Asn Gly Lys Leu Arg Gln Trp Leu Ile Asp Gln Ile
                20                  25                  30

Asp Ser Gly Lys Tyr Pro Gly Leu Val Trp Glu Asn Glu Glu Lys Ser
            35                  40                  45

Ile Phe Arg Ile Pro Trp Lys His Ala Gly Lys Gln Asp Tyr Asn Arg
        50                  55                  60

Glu Glu Asp Ala Ala Leu Phe Lys Ala Trp Ala Leu Phe Lys Gly Lys
    65                  70                  75                  80

Phe Arg Glu Gly Ile Asp Lys Pro Asp Pro Pro Thr Trp Lys Thr Arg
                85                  90                  95
```

```
Leu Arg Cys Ala Leu Asn Lys Ser Asn Asp Phe Glu Glu Leu Val Glu
            100                 105                 110

Arg Ser Gln Leu Asp Ile Ser Asp Pro Tyr Lys Val Tyr Arg Ile Val
        115                 120                 125

Pro Glu Gly Ala Lys Lys Gly Ala Lys Gln Leu Thr Leu Glu Asp Pro
    130                 135                 140

Gln Met Ser Met Ser His Pro Tyr Thr Met Thr Thr Pro Tyr Pro Ser
145                 150                 155                 160

Leu Pro Ala Gln Gln Val His Asn Tyr Met Met Pro Pro Leu Asp Arg
                165                 170                 175

Ser Trp Arg Asp Tyr Val Pro Asp Gln Pro His Pro Glu Ile Pro Tyr
            180                 185                 190

Gln Cys Pro Met Thr Phe Gly Pro Arg Gly His His Trp Gln Gly Pro
        195                 200                 205

Ala Cys Glu Asn Gly Cys Gln Val Thr Gly Thr Phe Tyr Ala Cys Ala
    210                 215                 220

Pro Pro Glu Ser Gln Ala Pro Gly Val Pro Thr Glu Pro Ser Ile Arg
225                 230                 235                 240

Ser Ala Glu Ala Leu Ala Phe Ser Asp Cys Arg Leu His Ile Cys Leu
                245                 250                 255

Tyr Tyr Arg Glu Ile Leu Val Lys Glu Leu Thr Thr Ser Ser Pro Glu
            260                 265                 270

Gly Cys Arg Ile Ser His Gly Thr Tyr Asp Ala Ser Asn Leu Asp
        275                 280                 285

Gln Val Leu Phe Pro Tyr Pro Glu Asp Asn Gly His Arg Lys Asn Ile
    290                 295                 300

Glu Asn Leu Leu Ser His Leu Glu Arg Gly Val Val Leu Trp Met Ala
305                 310                 315                 320

Pro Asp Gly Leu Tyr Ala Lys Arg Leu Cys Gln Ser Thr Ile Tyr Trp
                325                 330                 335

Asp Gly Pro Leu Ala Leu Cys Asn Asp Arg Pro Asn Lys Leu Glu Arg
            340                 345                 350

Asp Gln Thr Cys Lys Leu Phe Asp Thr Gln Gln Phe Leu Ser Glu Leu
        355                 360                 365

Gln Ala Phe Ala His His Gly Arg Ser Leu Pro Arg Phe Gln Val Thr
    370                 375                 380

Leu Cys Phe Gly Glu Glu Phe Pro Asp Pro Gln Arg Gln Arg Lys Leu
385                 390                 395                 400

Ile Thr Ala His Val Glu Pro Leu Leu Ala Arg Gln Leu Tyr Tyr Phe
                405                 410                 415

Ala Gln Gln Asn Ser Gly His Phe Leu Arg Gly Tyr Asp Leu Pro Glu
            420                 425                 430

His Ile Ser Asn Pro Glu Asp Tyr His Arg Ser Ile Arg His Ser Ser
        435                 440                 445

Ile Gln Glu
    450

(2) INFORMATION FOR SEQ ID NO:15:

(i) SEQUENCE CHARACTERISTICS:
        (A) LENGTH: 154 base pairs
        (B) TYPE: nucleic acid
        (C) STRANDEDNESS: single
        (D) TOPOLOGY: linear
```

-continued (ii) MOLECULE TYPE: DNA (genomic)

(xi) SEQUENCE DESCRIPTION: SEQ ID NO:15:

| TTTTCTCTCT ACAGTCACCT CCCTGTTTAC CAAAGATAAT CACAATAAGT CCAGTTTACT | 60 |
| TACAAAACAA GTTTAGTTAT TAGAGGAAAC TAAAACTTCA GGATTCAGTC CAGATAATTT | 120 |
| TTAAAAACTC TAAAACAATG GACAGGGCTA GAAT | 154 |

(2) INFORMATION FOR SEQ ID NO:16:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

| TGGGCTCGGC CTGGTGGGGC AGCCACAGCG GGACGCAGTA GTGAAAGTCC AGTTTACTTA | 60 |
| CAAAACAAGT TTAGT | 75 |

(2) INFORMATION FOR SEQ ID NO:17:

(i) SEQUENCE CHARACTERISTICS:
        (A) LENGTH: 122 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

| TGGGCTCGGC CTTGGTGGGG CAGCCACAGC GGGACGCAAG TAGTGAGGGC ACTCAGAACG | 60 |
| CCACTCAGCC CCGACAGGCA GGGCACGAGG AGGCAGCTCC TCACCCTCCC TTTCTCTTTT | 120 |
| GT | 122 |

(2) INFORMATION FOR SEQ ID NO:18:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

| TATTAGAGGA AACTAAAACT TCAGGATTCA GCAGGGCATG AGGAGGCAGC TCCTCACCCT | 60 |
| CCCTTTCTCT TTTGTAC | 77 |

IDENTIFICATION OF GENES ALTERED IN MULTIPLE MYELOMA

The invention disclosed herein was made with Government support under NIH Grant No. CA 44025. Accordingly, the U.S. Government has certain rights in this invention.

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Multiple myeloma (MM) is an incurable B cell tumor affecting B cell end-stage differentiation. Clinically, the course of MM is similar to end-stage plasma cell leukemia (PCL), i.e., there is an uncontrollable proliferation of myeloma cells accompanied by numerous complications, including hyperviscosity syndromes, hypercalcemia, infections, multiple bone fractures, and organ failure.

Non-random chromosomal translocation is known to play a crucial role in the tumorigenesis of hematologic malignancies (1). In B-cell lymphomas, many important proto-oncogenes deregulated by juxtaposition to immunoglobulin (Ig) gene locus have been identified. Each proto-oncogene is associated with a specific subtype of lymphoma, such as c-MYC in Burkitt's lymphoma, Cyclin DI IBCLI in mantle cell lymphoma, BCL-2 in follicular lymphoma and BCL-6 in diffuse large cell lymphoma (2–8). In contrast, little is known about molecular alterations of human MM/PCL, due to the difficulty in cytogenetic analysis. However, previous cytogenetic reports have shown a 14q+ chromosome, suggesting the existence of a chromosomal translocation involving the Ig heavy chain (IgH) locus, is observed in 20~30% of the MM/PCL cases and it is the most frequent consistent abnormality (9–12). Even in such cases, most cytogenetic data have failed to identify donor chromosomes other than 11q13, 8q24, and 18q21, where proto-oncogenes Cyclin DIIBCL-IIPRADI, c-MYC and BCL-2 are located, respectively. Among them, the 11q13 locus has been demonstrated to be involved in nearly 5~10% of the cases and also in 62% of the established cell lines (13). The t(11;14) (q13;q32) translocation is also accompanied by a corresponding overexpression of the Cyclin Dl gene, which raises a strong possibility of the involvement of this gene, although the breakpoints at 11q13 do not cluster like those of the lymphoma cases (14–16). Recent advances in fluorescence in situ hybridization (FISH) have made it possible to clarify both the frequency of the 14q+ chromosomes and the partner chromosomes of the IgH loci. One such report revealed an intriguing result, i.e., that numerous chromosomal loci are able to translocate to IgH locus, including 6p21, 1q21, 3p11, 7q11, 11q23 (17). This has prompted a search for the proto-oncogenes deregulated by the regulatory elements of the IgH gene for a further understanding of the molecular mechanisms of MM/PCL. In the present study, one candidate proto-oncogene, MUM1 (multiple myeloma oncogene 1), was found juxtaposed to the IgH gene as a result of t(6;14)(p25; q32) translocation in human myeloma cell line, SKMM-1. Over expression of the MUM1 mRNA was observed in this cell line. A second gene, called MUM-2 was found translocated in proximity to the IgH gene on chromosome 14q32 in human myeloma cell line, U-266.

The method of analysis of 14q+ chromosomal translocations and identification of the genes altered in multiple myeloma of this invention are useful since 1) no method is currently available to determine the chromosomal sequences involved in 14q+ translocations, the most important cytogenetic lesions associated with MM pathogenesis; 2) no specific gene lesion is currently known for MM; 3) no diagnostic method based on gene/DNA lesion is currently available for MM and 4) there are no therapeutic approaches aimed at counteracting the action of abnormal gene products in MM.

SUMMARY OF THE INVENTION

This invention provides a method of determining a chromosomal breakpoint in a subject suffering from multiple myeloma which comprises steps of: (a) obtaining a DNA sample from the subject suffering from multiple myeloma; (b) determining whether there is J and C disjunction in the immunoglobulin heavy chain gene in the obtained DNA sample; (c) obtaining a genomic library having clones which contain genomic DNA fragments from the DNA sample which shows positive J and C disjunction; (d) selecting and isolating clones of the obtained library which show positive hybridization with a probe which is capable of specifically hybridizing with the C but not the J region of the immunoglobulin heavy chain gene; (e) preparing fluorescent probes from the genomic DNA fragments of the isolated clones from step (d); (f) hybridizing said fluorescent probes with metaphase chromosomes; and (g) determining the identity of the chromosomes which are capable of hybridizing to said fluorescent probes, wherein the identification of a chromosome other than chromosome 14 would indicate that the chromosomal breakpoint is between chromosome 14 and the identified chromosome, thereby determining a chromosomal breakpoint in a subject suffering from multiple myeloma.

This invention provides a method to identify a gene other than the immunoglobulin gene which is located in chromosome 14, altered by a chromosomal breakpoint detected in a subject suffering from multiple myeloma which comprises steps of: a) selecting a probe having a sequence of a chromosome other than chromosome 14, identified at the chromosomal breakpoint detected in a subject suffering fron multiple myeloma, wherein said probe is capable of hybridizing to the unique sequence of the gene other than the immunoglobulin gene altered by a chromosomal breakpoint detected in a subject suffering from multiple myeloma; b) contacting said probe with mRNA isolated from a cell under conditions permitting formation of a complex between said probe and the mRNA; c) isolating the complex resulting from step (b); d) determining the sequence of the mRNA in the isolated complex, thereby determining the identity of the gene.

This invention provides a gene designated MUM-1. This invention provides a gene designated MUM-2. This invention provides an isolated nucleic acid molecule encoding a MUM protein. This invention provides a DNA encoding a MUM protein. This invention provides a cDNA encoding a MUM protein. This invention provides a genomic DNA molecule encoding a MUM protein. This invention provides a RNA molecule encoding a MUM protein. This invention provides an isolated nucleic acid molecule encoding a human MUM-1 protein. This invention provides an isolated nucleic acid molecule encoding a human MUM-2 protein. This invention provides an isolated nucleic acid molecule encoding a MUM protein operatively linked to a promoter of RNA transcription. This invention provides a vector comprising the an isolated cDNA encoding a MUM protein. This invention provides a vector which comprises an isolated cDNA encoding a MUM protein. This invention provides a vector which comprises an isolated cDNA encoding a MUM protein, wherein the vector is a plasmid. This invention provides a host cell for the vector which comprises an isolated cDNA encoding a MUM protein.

This invention provides a nucleic acid probe comprising a nucleic acid molecule of at least 15 nucleotides capable of specifically hybridizing with a unique sequence included within the sequence of a nucleic acid molecule encoding a MUM protein. This invention provides a nucleic acid probe comprising a nucleic acid molecule of at least 15 nucleotides which is complementary to a sequence of the isolated nucleic acid molecule encoding a MUM protein.

This invention provides a nucleic acid probe comprising a nucleic acid molecule of at least 15 nucleotides which is complementary to a sequence of the isolated nucleic acid molecule encoding a MUM protein which is linked to a nucleic acid sequence complementary to a sequence of a nucleic acid molecule of human chromosome 14.

This invention provides a nucleic acid probe comprising a the sequence of a nucleic acid molecule encoding a MUM-1 protein which is linked at a specific break point to a specified nucleic acid sequence of human chromosome 14. This invention provides a nucleic acid probe comprising a the sequence of a nucleic acid molecule encoding a MUM-2 protein which is linked at a specific break point to a specified nucleic acid sequence of human chromosome 14.

This invention provides a method for detecting a predisposition to multiple myeloma associated with the expression of a human MUM-1 protein in a sample from a subject which comprises detecting in a sample from the subject a rearrangement of nucleic acid encoding MUM-1 protein. This invention provides a method for detecting a predisposition to multiple myeloma associated with the expression of a human MUM-2 protein in a sample from a subject which comprises detecting in a sample from the subject a rearrangement of nucleic acid encoding MUM-2 protein.

This invention provides an antisense oligonucleotide having a sequence capable of specifically hybridizing to an mRNA molecule encoding a human MUM-1 protein so as to prevent overexpression of the mRNA molecule. This invention provides an antisense oligonucleotide having a sequence capable of specifically hybridizing to an mRNA molecule encoding a human MUM-2 protein so as to prevent overexpression of the mRNA molecule.

This invention provides an antisense oligonucleotide having a sequence capable of specifically hybridizing to an isolated cDNA molecule encoding a MUM protein. This invention provides an antisense oligonucleotide having a sequence capable of specifically hybridizing to the isolated genomic DNA molecule encoding a MUM protein. This invention provides an antisense oligonucleotide having a sequence capable of specifically hybridizing to an isolated RNA molecule encoding a MUM protein.

This invention provides a purified MUM protein. This invention provides a purified MUM-1 protein. This invention provides an antibody directed to a purified MUM-1 protein. This invention provides an antibody capable of specifically recognizing MUM-1 protein. This invention provides a purified MUM-2 protein. This invention provides an antibody directed to a purified MUM-2 protein. This invention provides an antibody capable of specifically recognizing a MUM-2 protein.

This invention provides a pharmaceutical compositior comprising an amount of an oligonucleotide effective to prevent overexpression of a human MUM-1 protein and a pharmaceutically acceptable carrier capable of passing through a cell membrane. This invention provides a pharmaceutical composition comprising an amount of the oligonucleotide effective to prevent overexpression of a human MUM-2 protein and a pharmaceutically acceptable carrier capable of passing through a cell membrane.

BRIEF DESCRIPTION OF THE FIGURES

FIGS. 2A–B. Molecular cloning of the breakpoints of the t(6;14) translocation and germline walking at MUM1 locus. (FIG. 2A) Restriction maps of $\lambda$SKB-4a and $\lambda$SKS-3 clones representing derivative 6 and 14 are shown, together with germline maps of IgH locus at 14q32 and MUM1 locus at 6p25. Arrows indicate the chromosomal breakpoints. B, BamHI; E, EcoRI; H, HindIII. (FIG. 2B) Comparison of the nucleotide sequences around the breakpoints on derivative 6 SEQ ID NO: 16 and derivative 14 SEQ ID NO: 17 chromosome. Homologous regions are indicated by dashes. The arrow indicates the breakpoint SEQ ID NO: 15. Nucleotide SEQ ID NO: 17 numbers shown below are the same as in the S$\mu$ sequence reported by Sun, et al. (18).

FIGS. 3A–B. Mapping of the MUM1 locus to chromosome 6p25. (FIG. 3A) $\lambda$MUM-3 genomic clone (FIG. 2A) was used as a probe for in situ hybridization. The white arrow indicates the fluorescence signal on chromosome 6 band p25. (FIG. 3B) Right panel shows the G-banding picture stained with DAPI.

(FIG. 4A) MUM1 RNA expression in various hematopoietic cell lines. MUM1 RNA is detected in B cell and mature T cell lines as a single 6 kb transcript. HELA, epithelial lineage; LCL, Epstein-Barr virus-transformed lymphoblastoid cell line; RAMOS and SK-MM-1, B-cell lineage; HUT-78 and MOLT-4, T-cell lineage; HL-60 and U937, myelomonocytic lineage; K562, erythroid lineage. Dashes indicate 28S and 18S. (FIG. 4B) Expression in B cell lines derived from various stages of B cell differentiation. MUM1 RNA is seen throughout the B cell development except for BJAB cell line. 697, pre-B cell stage; RAMOS and BJA-B, Burkitt cell line representing mature-B cell stage; RPMI-8226 and U-266, plasma cell stage. (FIG. 4C) Comparison of the expression level among myeloma cell lines. MUM1 RNA is overexpressed in SK-MM-1 cell line carrying t(6;14). Overexpression of the MUM1 is also demonstrated in XG-4, XG-7, and XG-10 cell lines. RPMI-8226, U-266, EJM, and SKMM-1 are IL-6 (interleukin-6) independent lines, whereas XG-1, XG-2, XG-4, XG-5, XG-6, XG-7, and XG-10 are IL-6 dependent lines.

(FIG. 5A) Restriction map of the MUM1 cDNA and the position of the open reading frame (box). The solid box indicates approximate position of the DNA binding domain. Sc, SacII; A, ApaI; P, PstI; H, HindIII; S, SacI (FIGS. 5B1–5B3) Nucleotide sequence of the MUM1 cDNA SEQ ID NO: 13 and corresponding amino acid sequence SEQ ID NO: 14. Putative translation initiation codons and preceding stop codons appearing in frame are underlined. The asterisk indicates the translation stop codon.

FIGS. 6A–B. Homology between MUM1 SEQ ID NO: 1 and other IRF family proteins SEQ ID NOS: 2–7. (FIG. 6A) Similarity at N-terminal DNA binding domain. Black background indicates identical residues found more than four times. Gray indicates conserved residues that appear in at least four sequences at a given position. Conserved tryptophan residues in DNA binding domain among IRF family members are indicated by closed circles. (FIG. 6B) Similarity at C-terminal region between human MUM1 SEQ ID NO: 8, Mouse LSIRF/Pip SEQ ID NO: 9, Human ICSBP SEQ ID NO: 10, Human ISGF3λ SEQ ID NO: 11, and Human IRF-3 SEQ ID NO: 12. Black and gray background are as in (A).

(FIG. 9A) The panel shows the results of Southern blot analysis of BamHI digested U-266 and normal control (placenta) genomic DNA using the indicated JH and Cα probes. The arrowheads indicate two DNA fragments containing Cα sequences not linked to JH sequences, suggesting the presence of a chromosomal breakpoint in 14q32. (FIG. 9B) The panel provides a schematic representation of the phage clones isolated from a library constructed from U-266 DNA and screened with a Cα probe. Based on restriction enzyme analysis, the three cloned regions represent a normal Cα region (14q32 germ-line), and two rearranged regions (der.14 and 14q32) containing unknown sequences linked to Cα sequences. The 2.5BE probe used for Northern blot analysis of MUM2 transcripts (FIG. 10) is also shown.

DETAILED DESCRIPTION OF THE INVENTION

Figure 1:
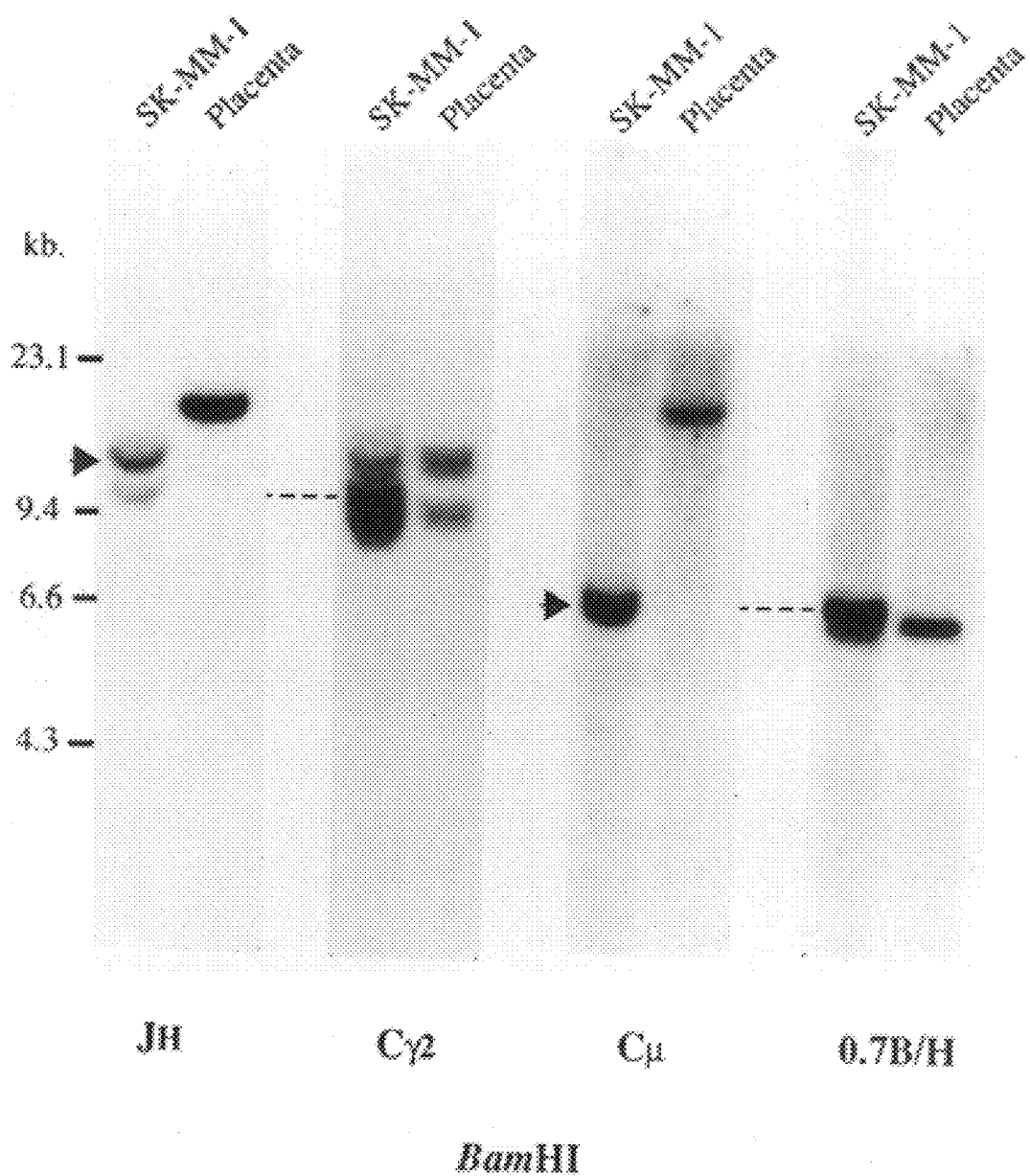
FIG. 1. JH-C$\mu$ dissociation in BamHI digested DNA of the 14q+ SK-MM-1 cell line. A 10 $\mu$g of the high molecular weight DNA was completely digested with BamHI, loaded on each lane and blotted. The same filter was sequentially hybridized with JH, C$\mu$, C$\gamma$2, and 0.7B/H probes. JH probe detects two rearranged bands of 12.0 kb and 9.7 kb. The 9.7 kb band is comigrated with that probed with C$\gamma$2 probe, suggesting it to be a physiological rearrangement. On the other hand, one allele of the C$\mu$ locus is deleted and another is rearranged (6.5 kb) without being comigrated with rearranged bands of JH. Therefore, 12.0 kb and 6.5 kb bands detected by JH and C$\mu$ (shown by arrowheads) might represent unknown derivative chromosome and derivative 14 chromosome, respectively. As expected, 0.7B/H probe (FIG. 2A) detected the rearranged band comigrated with 6.5 kb band of C$\mu$. Dashed lines show the combination. Size markers of $\lambda$/HindIII are shown on the left.

The following standard abbreviations are used throughout the specification to indicate specific nucleotides:

| C = cytosine | A = adenosine |
|---|---|
| T = thymidine | G = guanosine |

This invention provides a method of determining a chromosomal breakpoint in a subject suffering from multiple myeloma which comprises steps of: (a) obtaining a DNA sample from the subject suffering from multiple myeloma; (b) determining whether there is J and C disjunction in the immunoglobulin heavy chain gene in the obtained DNA sample; (c) obtaining a genomic library having clones which contain genomic DNA fragments from the DNA sample which shows positive J and C disjunction; (d) selecting and isolating clones of the obtained library which show positive hybridization with a probe which is capable of specifically hybridizing with the C but not the J region of the immunoglobulin heavy chain gene; (e) preparing fluorescent probes from the genomic DNA fragments of the isolated clones from step (d); (f) hybridizing said fluorescent probes with metaphase chromosomes; and (g) determining the identity of the chromosomes which are capable of hybridizing to said fluorescent probes, wherein the identification of a chromosome other than chromosome 14 would indicate that the chromosomal breakpoint is between chromosome 14 and the identified chromosome, thereby determining a chromosomal breakpoint in a subject suffering from multiple myeloma.

In an embodiment, step (b) of the above described method of this invention is performed by Southern blotting. In another embodiment, step (b) of the above method of this invention is performed by polymerase chain reaction (PCR) with appropriate probes. Polymerase chain reaction is well known in the art. Since the sequences of both the C and J regions of an immunoglobulin heavy chain gene are known, appropriate probes for PCR may routinely be designed.

In an embodiment, the genomic library is a phage vector library. In another embodiment, the genomic DNA fragments are generated by cleaving genomic DNA from cells of the subject with an appropriate restriction enzyme. In a further embodiment, the restriction enzyme is BamHI. In an embodiment, the restriction enzyme is Sau3AI. In another embodiment, the probe of step (d) is a human IgH J region JH probe. In a further embodiment, the probe of step (d) is a human IgH Cμ probe. In an embodiment, the probe of step (d) is a human IgH Cγ2 probe. In another embodiment, the chromosomal breakpoint identified is a t(6;14) (p25;q32) translocation. In an embodiment, the chromosomal breakpoint identified is a t(14;15) translocation.

This invention provides a method to identify a gene other than the immunoglobulin gene which is located in chromosome 14, altered by a chromosomal breakpoint detected in a subject suffering from multiple myeloma which comprises steps of: a) selecting a probe having a sequence of a chromosome other than chromosome 14, identified at the chromosomal breakpoint detected in a subject suffering from multiple myeloma, wherein said probe is capable of hybridizing to the unique sequence of the gene other than the immunoglobulin gene altered by a chromosomal breakpoint detected in a subject suffering from multiple myeloma; b) contacting said probe with mRNA isolated from a cell under conditions permitting formation of a complex between said probe and the mRNA; c) isolating the complex resulting from step (b); and d) determining the sequence of the mRNA in the isolated complex, thereby determining the identity of the gene.

In an embodiment, step (d) of the method to identify a gene other than the immunoglobulin gene which is located in chromosome 14, altered by a chromosomal breakpoint detected in a subject suffering from multiple myeloma comprises steps of: i) synthesizing complementary DNA to the mRNA; and ii) performing sequence analysis of the complementary DNA to determine the sequence of the mRNA.

This invention provides a gene identified by the method to identify a gene other than the immunoglobulin gene which is located in chromosome 14, altered by a chromosomal breakpoint detected in a subject suffering from multiple myeloma.

As used herein, "MUM" means any gene rearranged in 14q+ chromosomal abnormalities associated with multiple myeloma.

This invention provides a gene identified by the above method designated MUM-1. This invention provides a gene identified by the above method designated MUM-2.

This invention provides a gene identified by the above method, wherein the gene identified comprises a nucleic acid encoding a MUM protein. In an embodiment, the gene identified by the above method comprises a nucleic acid encoding a MUM-1 protein. In another embodiment, the gene identified by the above method comprises a nucleic acid encoding a MUM-2 protein.

This invention provides an isolated nucleic acid molecule encoding a MUM protein. In an embodiment, the isolated nucleic acid molecule encoding a MUM protein is a DNA molecule. In another embodiment, the isolated nucleic acid molecule encoding a MUM protein is a cDNA molecule.

In an embodiment, a cDNA nucleic acid molecule encoding a MUM-1 protein is cloned into a pBluescript KS+ and the resulting plasmid is designated as pcMUM1-1.6a (ATCC Accession No. 97579). Plasmid pcMUM1-1.6a was deposited on May 28, 1996 with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure. Plasmid pcMUM1-1.6a was accorded ATCC Accession Number 97579.

In another embodiment, a partial cDNA nucleic acid molecule encoding a MUM-1 protein is cloned into a peluescript KS+ and the resulting plasmid is designated as pMUM1-2.4B/N (ATCC Accession No. 97578). Plasmid pMUM1-2.4B/N was deposited on May 28, 1996 with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure. Plasmid pMUM1-2.4B/N was accorded ATCC Accession No. 97578.

In another embodiment, a partial cDNA nucleic acid molecule encoding a MUM-1 protein is cloned into a pBluescript KS+ and the resulting plasmid is designated as pMUM1-7.7B (ATCC Accession No. 97577). Plasmid pMUM1-7.7B was deposited or May 28, 1996 with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure. Plasmid pMUM1-7.7B was accorded ATCC Accession Number 97577.

In another embodiment, a partial cDNA of the nucleic acid molecule encoding a MUM-2 protein is cloned into a pBluescript KS+ and the resulting plasmid is designated as pMUM2-8 (ATCC Accession No. 97580). Plasmid pMUM2-8 was deposited on May 28, 1996 with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure. Plasmid pMUM2-8 was accorded ATCC Accession Number 97580.

In an embodiment, the isolated DNA molecule encoding a MUM protein is a cDNA molecule having the nucleotide sequence shown in FIG. 5B-3 (SEQ ID NO: 13).

In an embodiment, the isolated DNA molecule encoding a MUM protein is genomic DNA molecule. In an embodiment, the isolated nucleic acid molecule encoding a MUM protein is an RNA molecule.

In an embodiment, the isolated nucleic acid encodes a human MUM-1 protein. In another embodiment, the isolated nucleic acid molecule encodes a human MUM-2 protein.

In an embodiment, isolated nucleic molecule encodes the a human MUM-1 protein having substantially the same amino acid sequence as shown in FIG. 5B-2 (SEQ ID NO: 14). In an embodiment, isolated nucleic molecule encodes a human MUM-1 protein having the same amino acid sequence as shown in FIG. 5B (SEQ. ID NO). In an embodiment, the isolated nucleic acid molecule encoding a MUM protein is operatively linked to a promoter of RNA transcription.

This invention provides a vector comprising a cDNA molecule encoding a MUM protein. In an embodiment, a vector comprising cDNA encoding for MUM-1 is designated pcMUM1.6a. In an embodiment, a vector comprising partial cDNA encoding for MUM-1 is designated pMUM1.2.4B/N. In an embodiment, a vector comprising partial cDNA encoding for MUM-1 is designated pMUM1-7.7B. In an embodiment, a vector comprising partial cDNA encoding for MUM-2 is designated pMUM2-8. In an embodiment, a vector comprises genomic DNA encoding for MUM. In an embodiment, the vector is a plasmid. In an embodiment, a host cell comprises the vector comprising cDNA encoding for MUM. In an embodiment, a host cell comprises the vector comprising genomic DNA encoding for MUM. In a further embodiment, the host cell comprising vectors comprising cDNA encoding for MUM or comprising genomic DNA encoding for MUM is selected from a group consisting of a bacterial cell, a plant cell, and insect cell and a mammalian cell.

This invention provides a nucleic acid probe comprising a nucleic acid molecule of at least 15 nucleotides capable of specifically hybridizing with a unique sequence included within the sequence of a nucleic acid molecule encoding a MUM protein. This invention provides a nucleic acid probe comprising a nucleic acid molecule of at least 15 nucleotides which is complementary to a sequence of the isolated nucleic acid molecule encoding a MUM protein.

As used herein, the phrase "specifically hybridizing" means the ability of a nucleic acid molecule to recognize a nucleic acid sequence complementary to its own and to form double-helical segments through hydrogen bonding between complementary base pairs.

In an embodiment, the nucleic acid probe specifically hybridizes with nucleic acid encoding MUM-1. In an embodiment, the nucleic acid probe is complementary to nucleic acid encoding MUM-1. In an embodiment, the nucleic acid probe specifically hybridizes with nucleic acid encoding MUM-2. In an embodiment, the nucleic acid probe is complementary to nucleic acid encoding MUM-2.

In an embodiment, the nucleic acid probe which specifically hybridizes with nucleic acid encoding MUM-1 is a DNA probe. In an embodiment, the nucleic acid probe which specifically hybridizes with nucleic acid encoding MUM-2 is a DNA probe.

In an embodiment, the nucleic acid probe which specifically hybridizes with nucleic acid encoding MUM-1 is a RNA probe. In an embodiment, the nucleic acid probe which specifically hybridizes with nucleic acid encoding MUM-2 is a RNA probe.

In an embodiment, the nucleic acid probe which specifically hybridizes with nucleic acid encoding MUM-1 is a genomic DNA probe. In an embodiment, the nucleic acid probe which specifically hybridizes with nucleic acid encoding MUM-2 is a genomic DNA probe.

In an embodiment, the nucleic acid probe which specifically hybridizes with nucleic acid encoding MUM-1 is labeled with a detectable marker. In an embodiment, the nucleic acid probe which specifically hybridizes with nucleic acid encoding MUM-2 is labeled with a detectable marker.

In an embodiment, the detectable marker is selected from the group consisting of a radioactive isotope, enzyme, dye, biotin, a fluorescent label or a chemiluminescent label.

In an embodiment, the nucleic acid probe which specifically hybridizes with nucleic acid encoding MUM-1 is linked to a nucleic acid sequence capable of specifically hybridizing with a unique sequence included within the sequence of a nucleic acid molecule of human chromosome 14. In an embodiment, the nucleic acid probe which specifically hybridizes with nucleic acid encoding MUM-2 is linked to a nucleic acid sequence capable of specifically hybridizing with a unique sequence included within the sequence of a nucleic acid molecule of human chromosome 14.

This invention provides a nucleic acid probe comprising a nucleic acid molecule of at least 15 nucleotides which is complementary to a sequence of the isolated nucleic acid molecule encoding a MUM protein which is linked to a nucleic acid sequence complementary to a sequence of a nucleic acid molecule of human chromosome 14.

In an embodiment, the nucleic acid probe comprises a nucleic acid molecule of at least 15 nucleotides which is complementary to a sequence of the isolated nucleic acid molecule encoding a MUM-1 protein which is linked to a nucleic acid sequence complementary to a sequence of a nucleic acid molecule of human chromosome 14.

In an embodiment, the nucleic acid probe comprises a nucleic acid molecule of at least 15 nucleotides which is complementary to a sequence of the isolated nucleic acid molecule encoding a MUM-2 protein which is linked to a nucleic acid sequence complementary to a sequence of a nucleic acid molecule of human chromosome 14.

In an embodiment, the nucleic acid probe comprises a nucleic acid molecule of at least 15 nucleotides which is complementary to a sequence of the isolated nucleic acid molecule encoding a MUM-1 protein which is linked at a specific break point to a nucleic acid sequence complementary to a sequence of a nucleic acid molecule of human chromosome 14.

In an embodiment, the nucleic acid probe comprises a nucleic acid molecule of at least 15 nucleotides which is complementary to a sequence of the isolated nucleic acid molecule encoding a MUM-2 protein which is linked at a specific break point to a nucleic acid sequence complementary to a sequence of a nucleic acid molecule of human chromosome 14.

In an embodiment, the specific break point of the nucleic acid probe comprises a portion of the t(6;14) (p25;q32) translocation. In an embodiment, the specific break point of the nucleic acid probe comprises a portion of a t(14;15) translocation. In an embodiment, the nucleic acid probe comprising a portion of the t(6;14) (p25;q32) translocation is labeled with a detectable marker. In an embodiment, the nucleic acid probe comprising a portion of a t(14;15) translocation is labeled with a detectable marker. In an embodiment, the nucleic acid probe comprising a portion of the t(6;14) (p25;q32) or comprising a portion of a t(14;15) translocation has a detectable marker selected from the group consisting of a radioactive isotope, enzyme, dye, biotin, a fluorescent label or a chemiluminescent label.

This invention provides a method for detecting a predisposition to multiple myeloma associated with the expression of a human MUM-1 protein in a sample from a subject which comprises detecting in a sample from the subject a rearrangement of nucleic acid encoding MUM-1 protein.

This invention provides a method for detecting a predisposition to multiple myeloma associated with the expression of a human MUM-2 protein in a sample from a subject which comprises detecting in a sample from the subject a rearrangement of nucleic acid encoding MUM-2 protein.

In an embodiment, the rearrangement of nucleic acid encoding MUM-1 protein is detected by contacting the nucleic acid from the sample with a MUM-1 probe under conditions permitting the MUM-1 probe to hybridize with the nucleic acid encoding MUM-1 protein from the sample, thereby detecting the rearrangement of nucleic acid encoding MUM-1 protein in the sample.

In an embodiment, the rearrangement of nucleic acid encoding MUM-2 protein is detected by contacting the nucleic acid from the sample with a MUM-2 probe under conditions permitting the MUM-2 probe to hybridize with the nucleic acid encoding MUM-2 protein from the sample, thereby detecting the rearrangement of nucleic acid encoding MUM-2 protein in the sample.

In an embodiment, the rearrangement of nucleic acid encoding MUM-1 protein is detected by a MUM-1 probe comprising a nucleic acid molecule of at least 15 nucleotides which is complementary to a sequence of the isolated nucleic acid molecule encoding MUM-1 protein which is linked to a nucleic acid sequence complementary to a sequence of a nucleic acid molecule of human chromosome 14.

In an embodiment, the rearrangement of nucleic acid encoding MUM-2 protein is detected by a the MUM-2 probe comprising a nucleic acid molecule of at least 15 nucleotides which is complementary to a sequence of the isolated nucleic acid molecule encoding MUM-2 protein which is linked to a nucleic acid sequence complementary to a sequence of a nucleic acid molecule of human chromosome 15.

In an embodiment, the MUM-1 probe comprising a nucleic acid molecule of at least 15 nucleotides which is complementary to a sequence of the isolated nucleic acid molecule encoding MUM-1 protein is linked at a specific break point to a nucleic acid sequence complementary to a sequence of a nucleic acid molecule of human chromosome 14.

In an embodiment, the MUM-2 probe comprising a nucleic acid molecule of at least 15 nucleotides which is complementary to a sequence of the isolated nucleic acid molecule encoding MUM-2 protein is linked at a specific break point to a nucleic acid sequence complementary to a sequence of a nucleic acid molecule of human chromosome 15.

In an embodiment, the MUM-1 probe comprises a specific break point comprising a portion of the t(6;14) (p25;q32) translocation. In an embodiment, the MUM-2 probe comprises a specific break point comprising a portion of a t(14;15) translocation.

In an embodiment, the method for detecting a predisposition to multiple myeloma associated with the expression of a human MUM-1 protein in a sample from a subject which comprises detecting in a sample from the subject a rearrangement of nucleic acid encoding MUM-1 protein comprises: a) obtaining DNA from the sample of the subject suffering from multiple myeloma; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human MUM-1 protein, wherein the sequence of a nucleic acid molecule encoding a MUM-1 protein is linked at a specific break point to a specified nucleic acid sequence of human chromosome 14 and labeled with a detectable marker; e) detecting labeled bands which have hybridized to the nucleic acid probe capable of specifically hybridizing with a unique sequence included within the sequence of a nucleic acid molecule encoding a human MUM-1 protein, wherein the sequence of a nucleic acid molecule encoding a MUM-1 protein is linked at a specific break point to a specified nucleic acid sequence of human chromosome 14 to create a unique band pattern specific to the DNA of subjects suffering from multiple myeloma; f) preparing DNA obtained from a sample of a subject for diagnosis by steps (a–e); and g) comparing the detected band pattern specific to the DNA obtained from a sample of subjects suffering from multiple myeloma from step (e) and the DNA obtained from a sample of the subject for diagnosis from step (f) to determine whether the patterns are the same or different and to diagnose thereby predisposition to multiple myeloma if the patterns are the same.

In an embodiment, the method for detecting a predisposition to multiple myeloma associated with the expression of a human MUM-2 protein in a sample from a subject which comprises detecting in a sample from the subject a rearrangement of nucleic acid encoding MUM-2 protein comprises: a) obtaining DNA from the sample of the subject suffering from multiple myeloma; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human MUM-2 protein, wherein the sequence of a nucleic acid molecule encoding a MUM-2 protein is linked at a specific break point to a specified nucleic acid sequence of human chromosome 14 and labeled with a detectable marker; e) detecting labeled bands which have hybridized to the nucleic acid probe capable of specifically hybridizing with a unique sequence included within the sequence of a nucleic acid molecule encoding a human MUM-2 protein, wherein the sequence of a nucleic acid molecule encoding a MUM-2 protein is linked at a specific break point to a specified nucleic acid sequence of human chromosome 14 to create a unique band pattern specific to the DNA of subjects suffering from multiple myeloma; f) preparing DNA obtained from a sample of a subject for diagnosis by steps (a–e); and g) comparing the detected band pattern specific to the DNA obtained from a sample of subjects suffering from multiple myeloma from stee (e) and the DNA obtained from a sample of the subject for diagnosis from step (f) to determine whether the patterns are the same or different and to diagnose thereby predisposition to multiple myeloma if the patterns are the same.

In an embodiment, the size fractionation in step (c) is effected by a polyacrylamide or agarose gel. In an embodiment, the detectable marker is radioactive isotope, enzyme, dye, biotin, a fluorescent label or a chemiluminescent label.

In an embodiment, the method for detecting a predisposition to multiple myeloma associated with the expression of a human MUM-1 protein in a sample from a subject which comprises detecting in a sample from the subject a rearrangement of nucleic acid encoding MUM-1 protein comprises: a) obtaining RNA from the sample of the subject suffering from multiple myeloma; b) separating the RNA sample by size fractionation; c) contacting the resulting RNA species with a nucleic acid probe capable of specifically hybridizing with a unique sequence included within the sequence of a nucleic acid molecule encodirg a human MUM-1 protein, wherein the sequence of a nucleic acid molecule encoding a MUM-1 protein is linked at a specific break point to a specified nucleic acid sequence of human chromosome 14 and labeled with a detectable marker; d) detecting labeled bands which have hybridized to the RNA species to create a unique band pattern specific to the RNA of subjects suffering from multiple myeloma; e) preparing RNA obtained from a sample of a subject for diagnosis by steps (a–d); and f) comparing the detected band patterr specific to the RNA obtained from a sample of subjecte suffering from multiple myeloma from step (d) and the RNA obtained from a sample of the subject for diagnosis from step (f) to determine whether the patterns are the same or different and to diagnose thereby predisposition to multiple myeloma if the patterns are the same.

In an embodiment, the method for detecting a predisposition to multiple myeloma associated with the expression of a human MUM-2 protein in a sample from a subject which comprises detecting in a sample from the subject a rearrangement of nucleic acid encoding MUM-2 protein comprises: a) obtaining RNA from the sample of the subject suffering from multiple myeloma; b) separating the RNA sample by size fractionation; c) contacting the resulting RNA species with a nucleic acid probe capable of specifically hybridizing with a unique sequence included within the sequence of a nucleic acid molecule encoding a human MUM-2 protein, wherein the sequence of a nucleic acid molecule encoding a MUM-2 protein is linked at a specific break point to a specified nucleic acid sequence of human chromosome 15 and labeled with a detectable marker; d) detecting labeled bands which have hybridized to the RNA species to create a unique band pattern specific to the RNA of subjects suffering from multiple myeloma; e) preparing RNA obtained from a sample of a subject for diagnosis by steps (a–d); and f) comparing the detected band pattern specific to the RNA obtained from a sample of subjects suffering from multiple myeloma from step (d) and the RNA obtained from a sample of the subject for diagnosis from step (f) to determine whether the patterns are the same or different and to diagnose thereby predisposition to multiple myeloma if the patterns are the same.

In an embodiment, the size fractionation in step (b) is effected by a polyacrylamide or agarose gel. In an embodiment, the detectable marker is radioactive isotope, enzyme, dye, biotin, a fluorescent label or a chemiluminescent label.

In an embodiment, multiple myeloma associated with the expression of a specific human MUM-1 is diagnosed by the method for detecting a predisposition to multiple myeloma associated with the expression of a human MUM-1 protein in a DNA or RNA sample from a subject which comprises detecting in a sample from the subject a rearrangement of nucleic acid encoding MUM-1 protein.

In an embodiment, multiple myeloma associated with the expression of a specific human MUM-2 is diagnosed by the method for detecting a predisposition to multiple myeloma associated with the expression of a human MUM-12 protein in a DNA or RNA sample from a subject which comprises detecting in a sample from the subject a rearrangement of nucleic acid encoding MUM-2 protein.

This invention provides an antisense oligonucleotide having a sequence capable of specifically hybridizing to an mRNA molecule encoding a human MUM-1 protein so as to prevent overexpression of the mRNA molecule. This invention provides an antisense oligonucleotide having a sequence capable of specifically hybridizing to an mRNA molecule encoding a human MUM-2 protein so as to prevent overexpression of the mRNA molecule.

This invention provides an antisense oligonucleotide having a sequence capable of specifically hybridizing to the cDNA molecule encoding a MUM protein. This invention provides an antisense oligonucleotide having a sequence capable of specifically hybridizing to the genomic DNA molecule encoding a MUM protein. This invention provides an antisense oligonucleotide having a sequence capable of specifically hybridizing to the RNA molecule encoding a MUM protein.

This invention provides a purified MUM protein. This invention provides a purified MUM-1 protein. This invention provides a purified human MUM-1 protein. This invention provides an antibody directed to a purified MUM-1 protein. This invention provides an antibody capable of specifically recognizing MUM-1 protein. In an embodiment, the antibody capable of specifically recognizing MUM-1 protein is a human MUM-1 protein.

This invention provides a purified MUM-2 protein. This invention provides a purified human MUM-2 protein. This invention provides an antibody directed to a purified MUM-2 protein. This invention provides an antibody capable of specifically recognizing MUM-2 protein. In an embodiment, the antibody capable of specifically recognizing MUM-2 protein is a human MUM-2 protein.

In an embodiment, the antibody directed to a purified MUM-1 protein is a monoclonal antibody. In an embodiment, the antibody capable of specifically recognizing MUM-1 protein is a monoclonal antibody. In an embodiment, the antibody capable of specifically recognizing MUM-1 protein is a human MUM-1 protein.

In an embodiment, the antibody directed to a purified MUM-2 protein is a monoclonal antibody. In an embodiment, the antibody capable of specifically recognizing MUM-2 protein is a monoclonal antibody. In an embodiment, the antibody capable of specifically recognizing MUM-2 protein is a human MUM-2 protein.

This invention provides a pharmaceutical composition comprising an amount of the oligonucleotide having a sequence capable of specifically hybridizing to an mRNA molecule encoding a human MUM-1 protein so as to prevent overexpression of the mRNA molecule effective to prevent overexpression of a human MUM-1 protein and a pharmaceutically acceptable carrier capable of passing through a cell membrane.

This invention provides a pharmaceutical composition comprising an amount of the oligonucleotide having a sequence capable of specifically hybridizing to a cDNA molecule encoding a MUM protein effective to prevent overexpression of a human MUM-1 protein and a pharmaceutically acceptable carrier capable of passing through a cell membrane.

This invention provides a pharmaceutical composition comprising an amount of the oligonucleotide having a sequence capable of specifically hybridizing to a genomic DNA molecule effective to prevent overexpression of a human MUM-1 protein and a pharmaceutically acceptable carrier capable of passing through a cell membrane.

This invention provides a pharmaceutical composition comprising an amount of the oligonucleotide having a sequence capable of specifically hybridizing to an mRNA molecule encoding a human MUM-2 protein so as to prevent overexpression of the mRNA molecule effective to prevent overexpression of a human MUM-2 protein and a pharmaceutically acceptable carrier capable of passing through a cell membrane.

This invention provides a pharmaceutical composition comprising an amount of the oligonucleotide having a sequence capable of specifically hybridizing to a cDNA molecule encoding a MUM protein effective to prevent overexpression of a human MUM-2 protein and a pharmaceutically acceptable carrier capable of passing through a cell membrane.

This invention provides a pharmaceutical composition comprising an amount of the oligonucleotide having a sequence capable of specifically hybridizing to a genomic DNA molecule effective to prevent overexpression of a human MUM-2 protein and a pharmaceutically acceptable carrier capable of passing through a cell membrane.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

Cell Lines.

The following myeloma cell lines were used in the present study: SK-MM-l, RPMI-8226, U266, EJM, XG-1, XG-2, XG-4, XG-5, XG-6, XG-7, and XG-10. The RPMI-8226 cell line was obtained through the American Type Culture Collection (ATCC, Rockville, Md.). SKMM-1 and U-266 cell lines were gifts from Dr. A. N. Houghton and Dr. K. Nilsson, respectively (18; 12). Characterization of these cell lines were previously reported. Six XG cell lines were gifts from Dr. B. Klein and were cultured in RPMI 1640 containing 10% fetal calf serum (FCS), SxlO-smol/L 2-ME, and rIL-6 (lng/mL)(13;19). Other myeloma cell lines used were all IL-6 independent. The SK-MM-l cell line was used to isolate the chromosomal breakpoint carrying the 14q+ chromosome without any information on the donor chromosome. XG-1, XG-2, XG-6, XG-8 cell lines are reported to carry the t(11;14)(q13;q32) translocation. XG-5 cells also share both t(11;14) and t(8;14)(q24;q32).

Southern and Northern Blot Analyses.

Southern blot analysis was performed as previously described (21). Briefly, ten micrograms of high molecular-weight DNA extracted from each cell line was digested to completion with BamHI and HindIII restriction enzymes, size-fractionated on 0.7% agarose gel, and transferred onto Duralose nitrocellulose membrane (Stratagene) according to the manufacturer's instructions. Blots were hybridized with a random-primed DNA probe and washed at 60° C. in 0.2xSSC and 0.1% SDS for 5 minutes. Genomic probes used in this study were as follows; human IgH J region JH probe (6.6 kb BamHI-HindIII fragment) was provided by Dr. J. V. Ravetch, human IgH $C\mu$ probe (1.3 kb EcoRI fragment) was provided by Dr. S. J. Korsmeyer. Human IgH region $C\gamma2$ probe was provided by Dr. C. Croce.

Northern blot analysis was performed as described previously (21). Briefly, a 10 $\mu g$ aliquot of total RNA was loaded on each lane and probed with a 2.1H probe of the MUMI gene (FIG. 2A). GAPDH or $\beta$-actin probes were used as controls for amount of total RNA.

Genomic Library.

High molecular-weight DNA of SK-MM-1 cell line was digested completely with BamHI and partially with Sau3AI, and size-fractionated by using a low-melting point agarose gel. DNA ranging from 10 kb to 23 kb were purified and ligated into the BamHI sites of $\lambda$-DASH II phage vector (Stratagene, La Jolla, Calif.). After packaging, $3\times10^5$ and $6\times10^5$ recombinant clones of the BamHI digested library and partially digested library were screened with JH and $C\mu$ probes, respectively. To isolate the germline region of the 6p25 locus, a commercially available human placental library (Stratagene) was screened. Positive clones were mapped with restriction enzymes by partial digestion of the phage DNAs followed by probing with T7 and T3 primers labeled with T4 polynucleokinase and 32p-$\gamma$ATP.

cDNA Library.

A phage library constructed by oligo-dT and random-priming normal human spleen RNA (Clontech) was screened by 2.1H probe (FIG. 2A) to isolate initial MUM1 cDNA clones. After the first round of screening, positive clones were used as probes to walk to the 5' side using the same library. Positive clones were subcloned into pBluescript and analyzed for mapping and sequencing.

DNA Sequencing.

DNA sequences were determined by the dideoxy chain termination method and analyzed by an ABI(Applied Biosystems) autosequencer. Deletion mutants for sequencing were prepared using exonuclease III and mung bean nuclease. cDNA sequences were analyzed with the Genetics Computer Group (GCG) programs. Sequence homology searches were carried out through the BLAST E-mail server at the National Center for Biotechnology Information, National Library of Medicine, Bethesda, Md.

Fluorescence in situ Hybridization (FISH).

Metaphase chromosome from human lymphocytes were prepared. A biotin-labeled probe was prepared by nick-translation using Bio-16-dUTP. Conditions for hybridization and washing were described previously (22).

Experimental Results

IgH Gene Rearrangement of the SK-MM-I Cell Line.

In BamHI digestion, the JH probe detects two rearranged bands of the size of 12.0 kb and 9.7 kb (FIG. 1). The 9.7 kb band is comigrated with that probed with $C\gamma2$ probe, suggesting it to be a physiological rearrangement, although this cell line secretes only $\lambda$ chain. One allele of the $C\mu$ locus is deleted and another is rearranged (6.5 kb) without being comigrated with rearranged bands of JH. Hybridization with a $C\alpha$ probe showed only the germline band (data not shown). These results suggested the possibility of the chromosomal breakpoint between JH and $C\mu$ locus. Hence, the 12.0 kb and the 6.5 kb bands detected by JH and $C\mu$ were considered to represent unknown derivative chromosome and derivative 14 chromosome, respectively.

Molecular Cloning of the t(6;14) (p25;q32) Breakpoint.

A genomic library constructed with BamHI complete digestion was screened with a JH probe to isolate the 12.0 kb BamHI band. Another library constructed with Sau3AI partial digestion was screened with a $C\mu$ probe to isolate phage clones containing the 6.5 kb BamHI fragment. Two phage clones, $\lambda$SKB-4a and $\lambda$ SKS-3, considered to represent the unknown derivative and derivative 14 chromosomes respectively, were obtained (FIG. 2A). A 0.7 kb BamHI-HindIII probe (0.7B/H) of the $\lambda$SKS-3 was used to confirm the combination with the rearranged 6.5 kb $C\mu$ band by Southern analysis (FIG. 1). The chromosomal origin of the centromeric side of the $\lambda$SKB-4a and telomeric side of the $\lambda$SKS-3 were confirmed by hybridization to a somatic cell hybrid DNA panel with a 4.5 kb ApaI fragment(4.5A) and 2.1 kb HindIII (2.1H) probes. Both probes showed positive signals in hybrid cell DNA containing a human chromosome 6 (data not shown). These probes were also used to isolate the germline chromosome 6 region by screening the human placental genomic library. One of the phage clone DNA ($\lambda$MUM-3) was used as a probe for FISH analysis. It identified the localization of this region to be chromosome 6 short arm p25 (FIG. 3). To investigate the precise breakpoint within the IgH gene, a 1.5 kb HindIII-EcoRI fragment of the $\lambda$SKS-3, containing the breakpoint on derivative 14 chromosome was sequenced. The breakpoint was confirmed to be just 3' to the switch $\mu$(S $\mu$) repetitive sequences SEQ ID NO: 15 (FIG. 2B). Nucleotide sequencing of the region around the breakpoints of chromosome 6 and derivative 6 chromosome showed that the chromosomal translocation was reciprocal with minimum deletion of both the IgH and 6p25 sequences.

Transcriptional Unit in the Vicinity of the 6p25 Breakpoint.

Figure 4A:
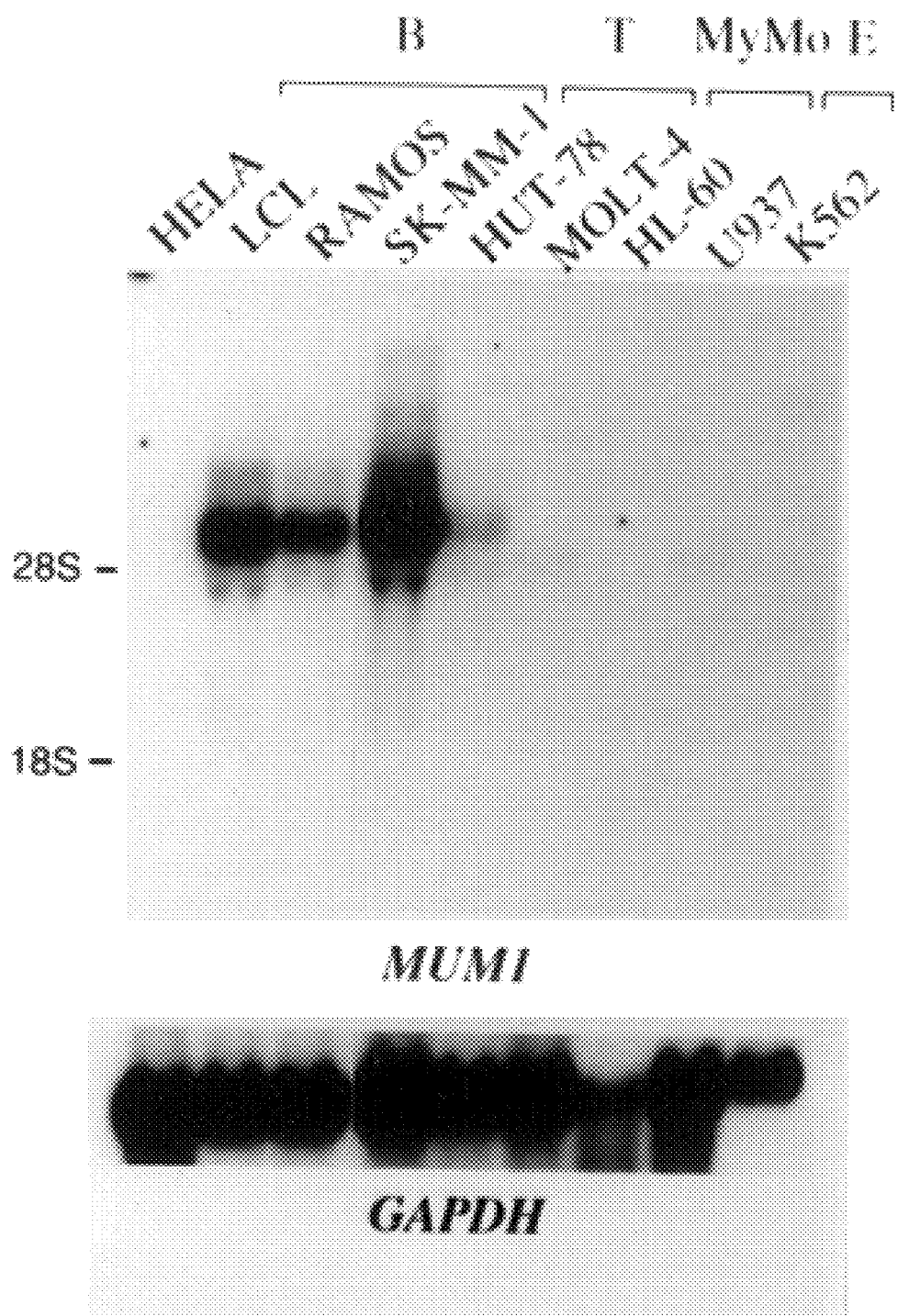
FIGS. 4A–C. Expression of the MUM1 gene in hematopoietic lineage. A 10 $\mu$g aliquot of total RNA was loaded on each lane and Northern blot analysis was performed using the 2.1H probe (FIG. 2A). GAPDH or $\beta$-actin probes were used to control for amount of RNA loaded.
Figure 4B:
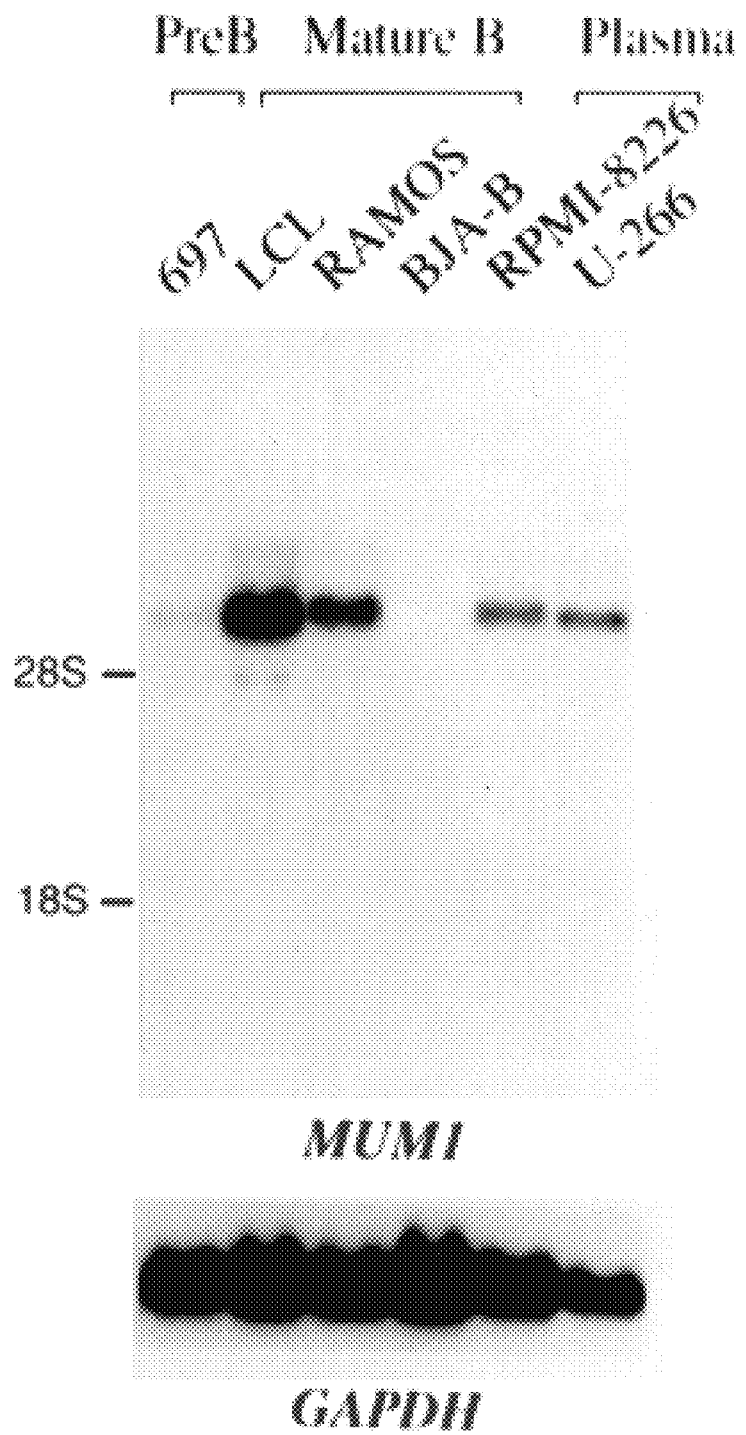
Figure 4C:
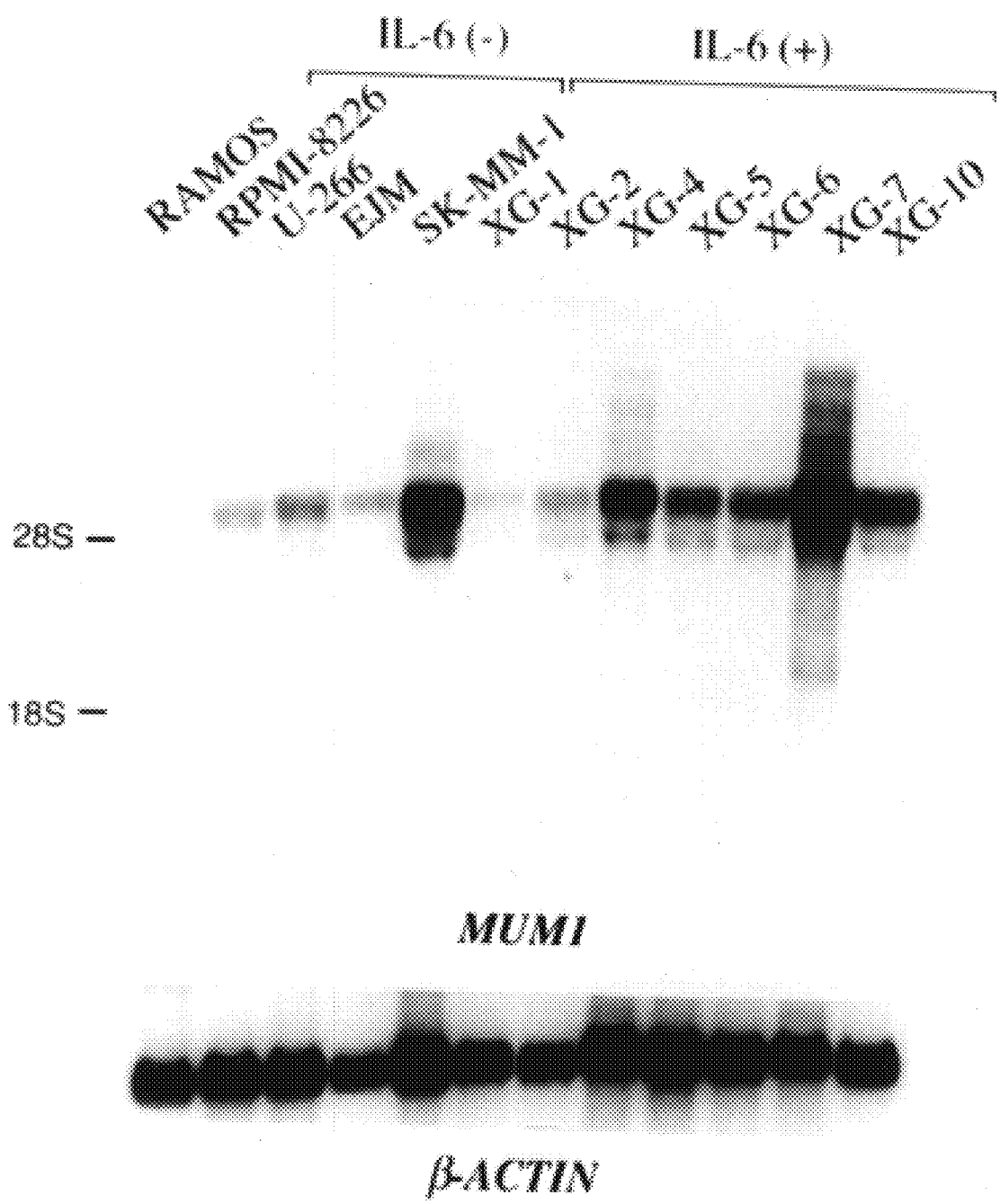

An attempt to find a functional transcriptional unit in the vicinity of the breakpoints was made. Although a 4.5A probe on derivative 6 chromosome could not detect any transcripts, a 2.1H probe on derivative 14 chromosome detected a single 6 kb transcript in the SK-MM-1 cell line. Accordingly, this gene was designated as MUM1 (multiple myeloma oncogene 1). The same probe was used to study the expression of the MUM1 gene in various hematopoietic cell lines. The 6 kb message was expressed at high levels in most B cell lines and at low levels in peripheral T cell lines (FIG. 4A). Cell lines derived from immature T cells, the myelomonocytic lineage, and erythroid lineage do not seem to express MUM1. In B cells, MUM1 appears to be expressed throughout the development from the preB cell stage to the plasma cell stage (FIG. 4B). However, some of the Burkitt's lymphoma derived cell lines such as BJA-B did not express this gene (data not shown). The expression level of the MUM1 transcript in myeloma cell lines was also examined (FIG. 4C). The SK-MM-1 cell line showed a 7.5-fold overexpression when compared with the other three IL-6 independent cell lines, suggesting a deregulated expression of the translocated allele. It is of interest that the IL-6 dependent XG-4, XG-7, and XG-10 cell lines are also expressing at high levels. Particularly, expression in the XG-7 cell line is 19.9 times the average of the aforementioned control cell lines.

MUM1 cDNA Cloning, Sequencing, and Homology Search.

Figure 5A:
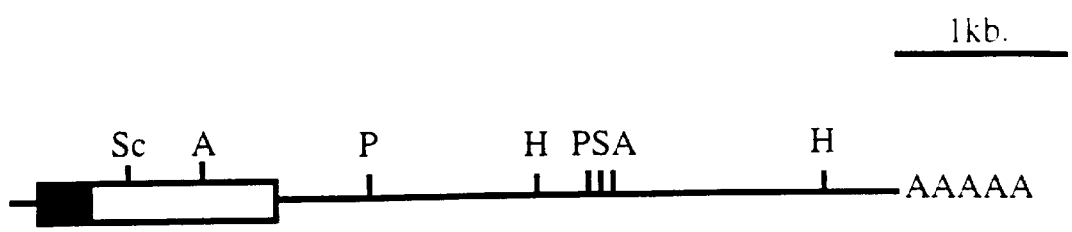
FIGS. 5A–B1–B3. Sequence of MUM1 cDNA and structure of its predicted protein product.

Human spleen cDNA library was initially screened with a 2.1H probe followed by three times walking to 5' side using cDNA probes. A 5.5 kb cDNA, approximately corresponding to the size detected by Northern analysis was isolated. This cDNA contained a 1,353 base pair open reading frame (ORF) and a long 3' untranslated region (FIG. 5A). The ORF encodes for a protein of 451 amino acids with a predicted molecular weight of 50 kD (FIG. 5B-1–5B-2 (SEQ ID NO: 14). The putative ATG initiation codon at position 217 has G at the −3 position which corresponds to the Kozak consensus sequence (23). The ORF is preceded by two in-frame stop codons. A database search demonstrated a significant similarity between MUM-1 ORF and the interferon regulatory factor (IRF) family proteins. The $NH_2$-terminal of the MUM-1 ORF (SEQ ID NO: 1) shares a high homology with all of the IRF family proteins (SEQ ID NOS: 2–7) which share a characteristic DNA binding motif consisting of the conserved 5 tryptophan residues (FIG. 6A). The COOH-terminal (SEQ ID NO: 8) also has a high homology with ICSBP (SEQ ID NO: 10) (interferon consensus sequence binding protein) (21), ISGF3γ (SEQ ID NO: 11) (interferon-stimulated gene factor-3 gamma) (22), and IRF-3 protein (SEQ ID NO: 12) (23) (FIG. 6B), although it did not have any homologous regions with IRF-1 and IRF-2 protein. The highest similarity (95.1%) and identity (SEQ ID NOS: 2 and 9) (91.8%) were found with a possible mouse homolog, LSIRF (lymphoid specific interferon regulatory factor)/Pip (PU-1 cofactor protein-1) (24, 25). A high similarity was found with ICSBP (63.98%), ISGF3γ (55.8%), and IRF3 (50.1%) among the human IRF family protein members. A gene sequence encoding a nearly identical protein was recently deposited in GenBank. This gene, termed ICSAT (interferon consensus sequence binding protein in adult T-cell leukemia cell lines or activated T cells) is likely to be the same gene as MUM1 (26).

Breakpoints at MUM1 Locus in Multiple Myeloma.

Figure 7:
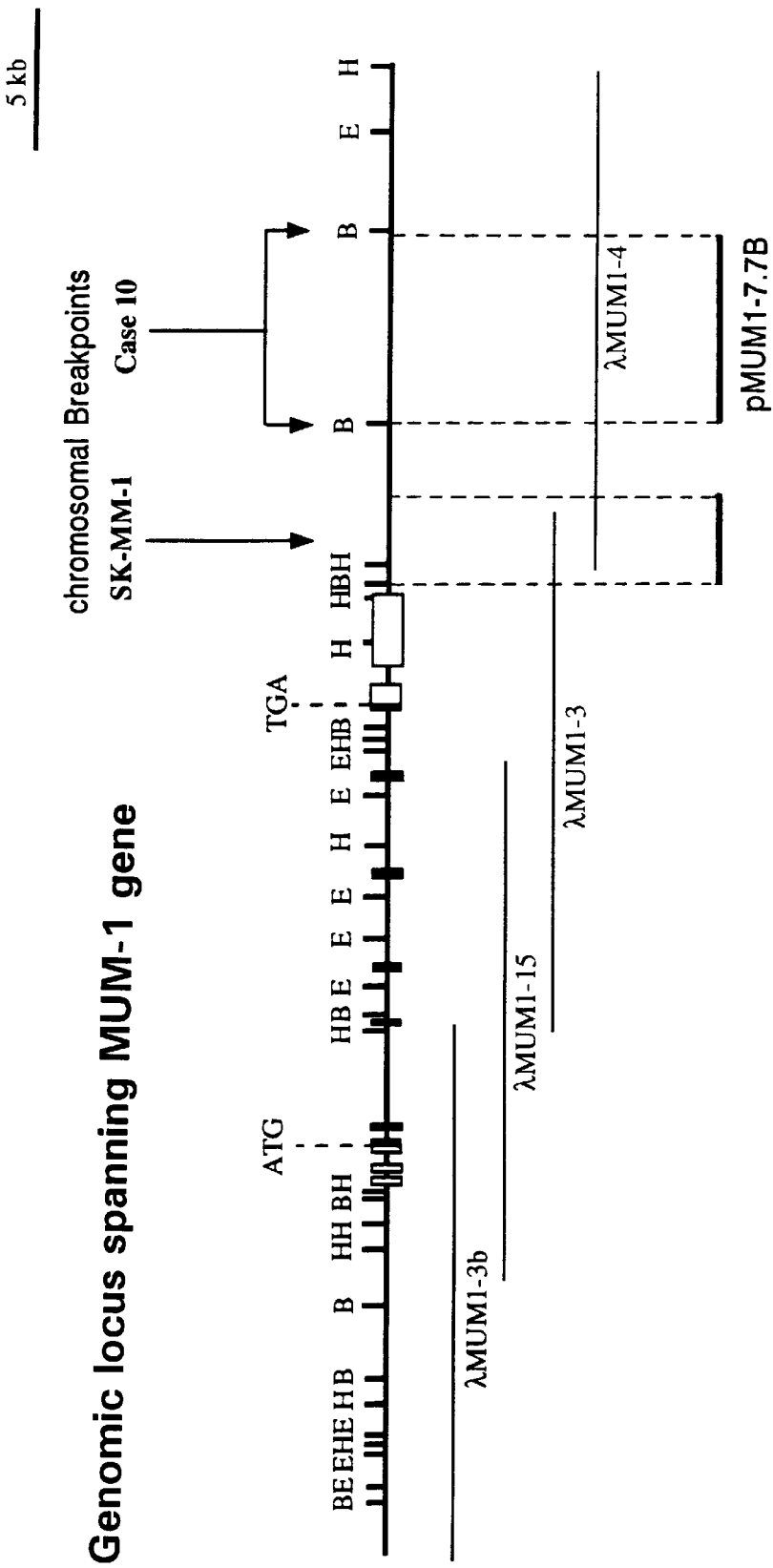
FIG. 7. Genomic organization of the MUM1 gene and location of the chromosomal breakpoints in multiple myeloma. Filled boxes indicate the coding regions and empty boxes indicate the noncoding regions. The position, and the size of each exon of the HUM1 gene are approximate and have been determined by the hybridizations. One exon in each restriction fragment may consist of more than two exons. Translation initiation codon (ATG) and stop codon (TGA) are indicated. Genomic probes used for further investigations are shown as solid bars below the map. Arrows indicate the chromosomal breakpoints of SKMM-1 cell line and case 10. B, BamHI; E, EcoRI; H, HindIII.
Figure 8:
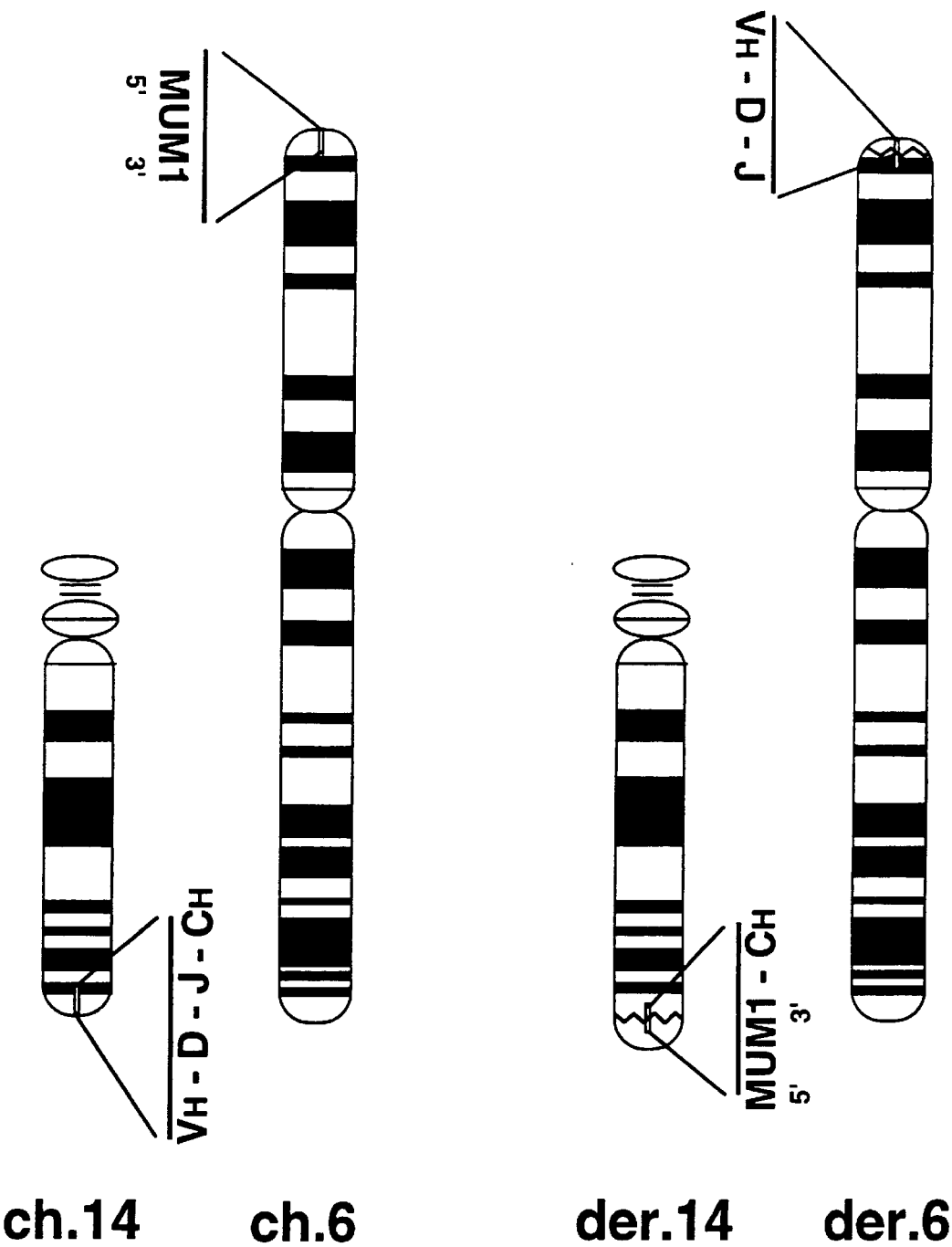
FIG. 8. Scheme of the t(6;14) (p25;q32) translocation involving the MUM1 and the immunoglobulin heavy chain (IgH) gene loci. VH-D-J-CH indicates variable-diversity joining-constant region of the IgH gene. Direction of the MUM1 gene on the chromosome 6 is tentatively drawn.

In order to analyze the exact location of the SK-MM-1 breakpoint at the 6p25 locus and to explore the frequency of the MUM1 gene involvement in myeloma cases, we walked nearly 55 kb in a human placental genomic phage library around the MUM1 gene and determined the rough exon-intron structure as shown in FIG. 7 (FIG. 7). The SK-MM-1 breakpoint was located 3' to the last exon, containing a poly A additional signal, consistent with an unaltered size of the MUM1 transcript of this cell line in Northern analysis. Seven repeat-free genomic probes shown in FIG. 7 have been used to investigate the rearrangement in Southern analyses of the 11 MM cell lines and 18 MM cases. One case (case 10) displayed rearranged bands in BamHI and XbaI digests when analyzed using a 0.9A probe located at 3' to the MUM1 gene.

Cloning of the MUM2 Locus from the U-266 Multiple Myeloma Cell Line.

Figure 9A:
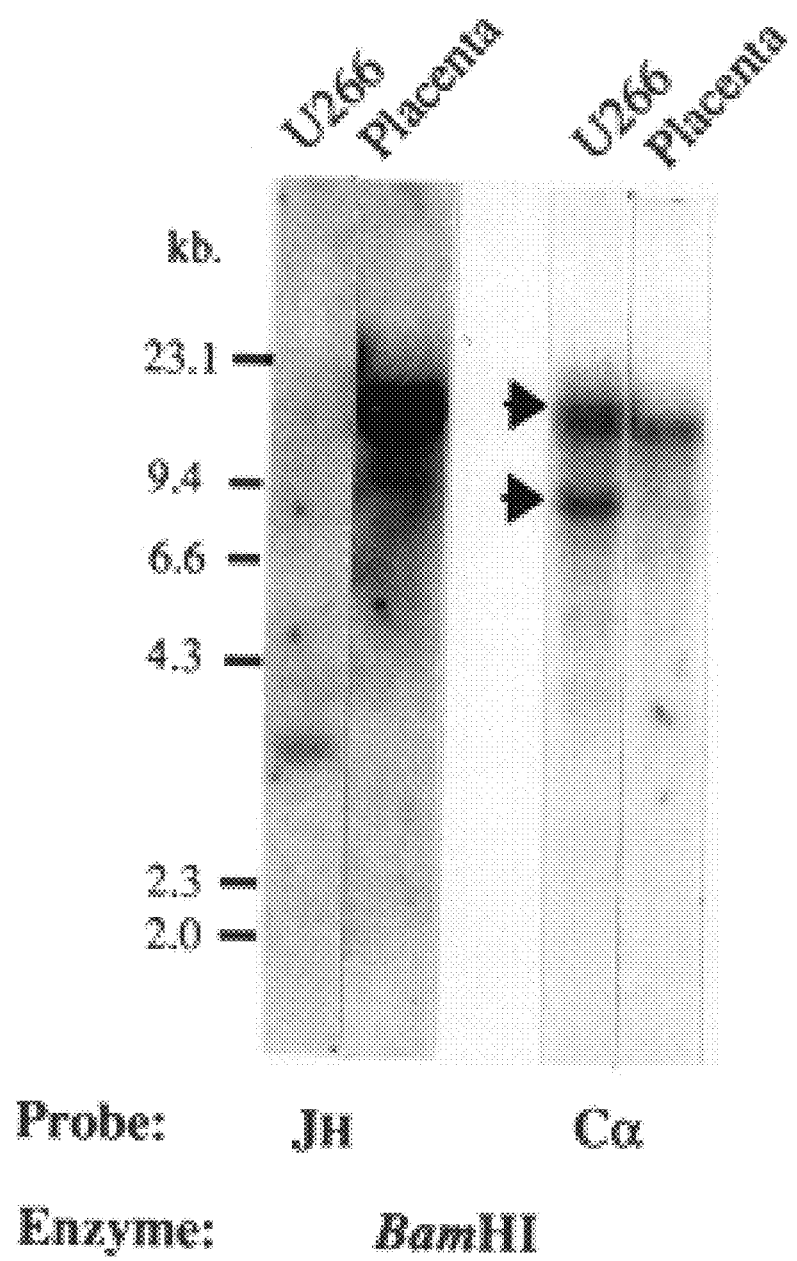
FIGS. 9A–B. Demonstration of JH-Cα disjunction in U-266 cells and cloning of normal and 14q+ chromosomal breakpoints.
Figure 9B:
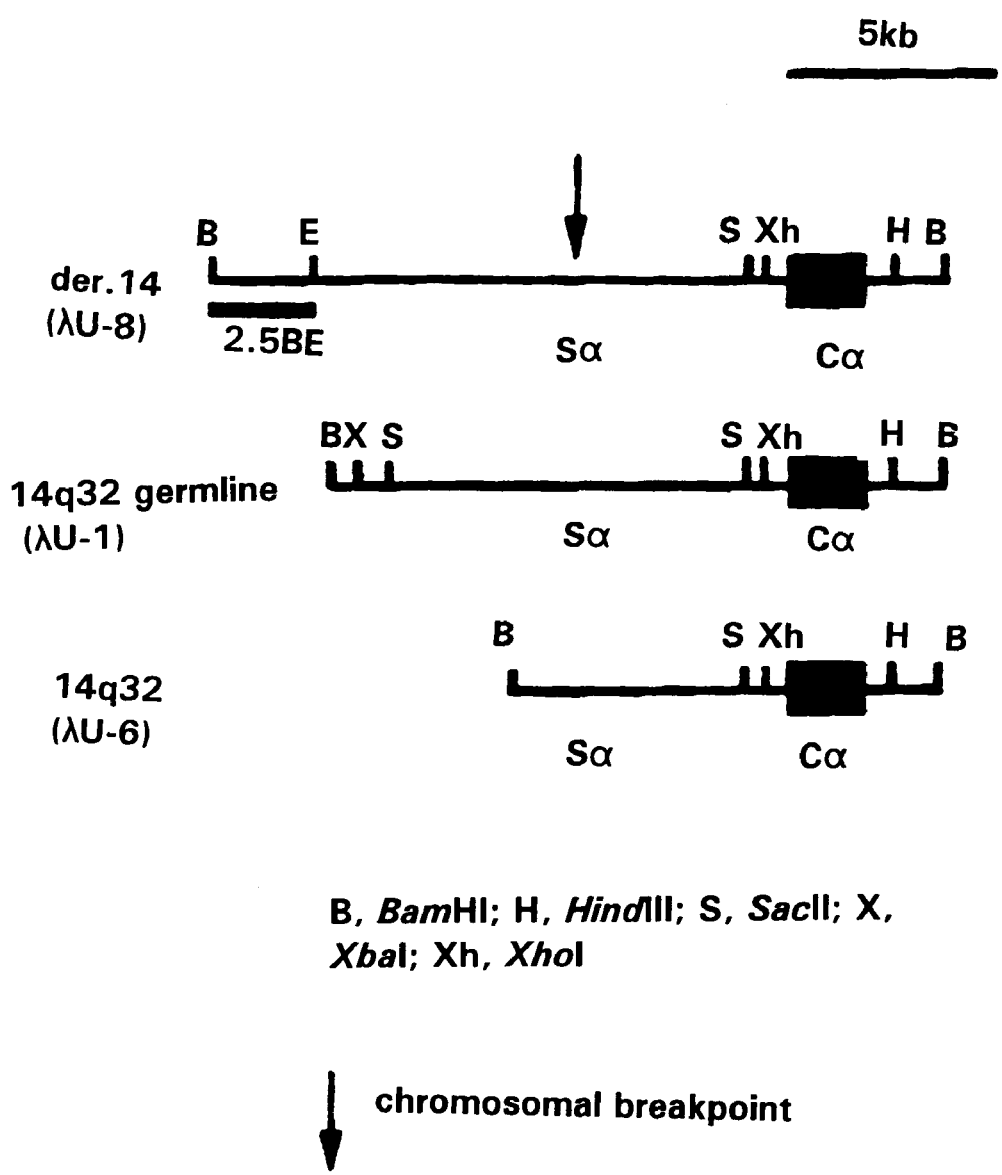
Figure 10:
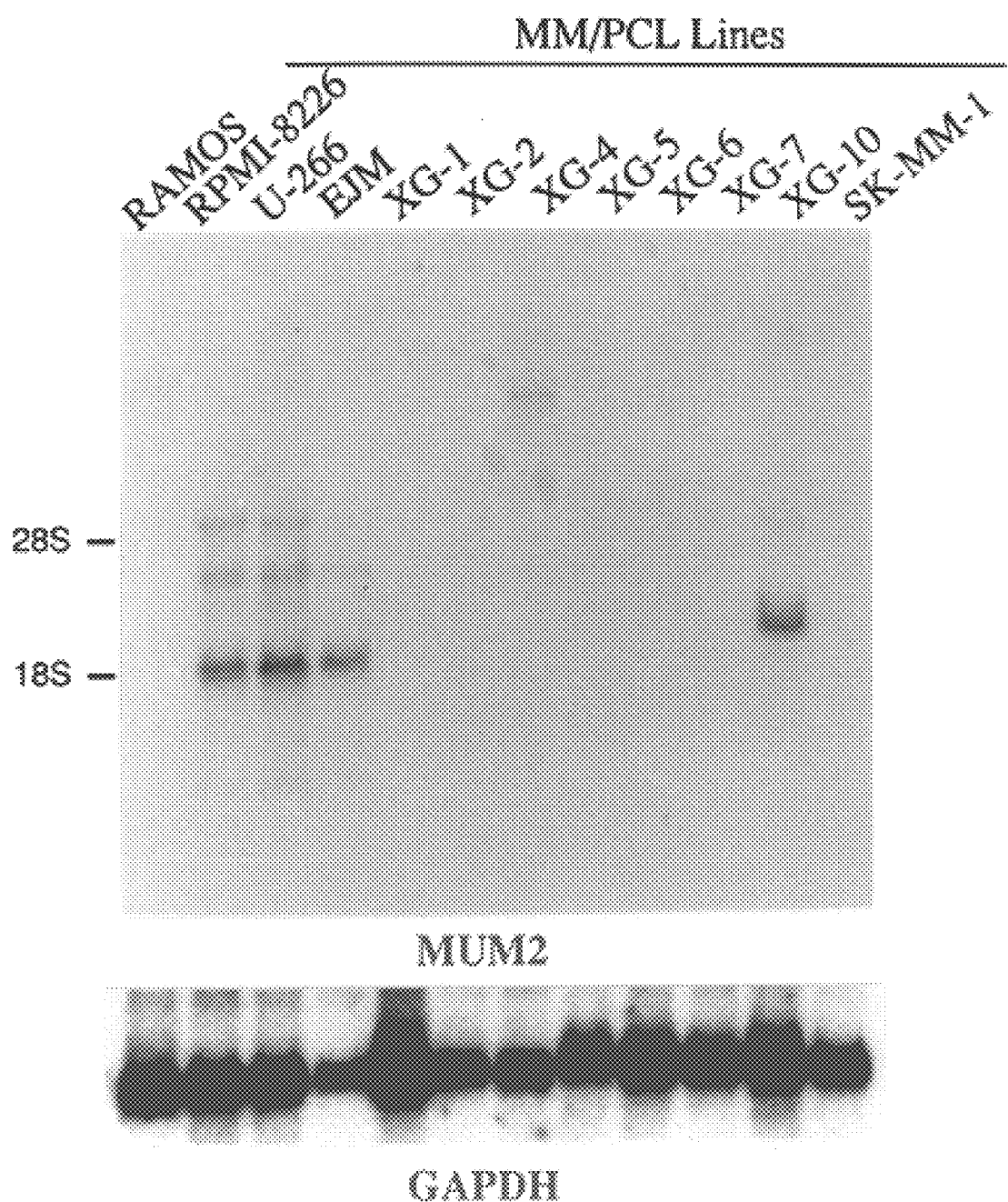
FIG. 10. Identification of MUM2 RNA transcripts. The figure shows the results of a Northern blot analysis of RNA extracted from various MM/PCL cell lines using the 2.5BE probe (see FIG. 9) or GAPDH probe (as a control for RNA loading). A 1.9 Kb RNA transcript is detectable in some cell lines including U-266, indicating that the 2.5BE fragments represents part of a gene, MUM2.

Using an experimental strategy analogous to the one described for the cloning of the MUM1 gene from the SK-MM-1 cell line, a second genetic locus altered in multiple myeloma (MUM2) was identified by analyzing the U-266 multiple myeloma cell line. Briefly, Southern blot analysis using BamH restriction digestion and various Ig probes showed that U-266 DNA contained two rearranged fragments (shown by arrowheads in FIG. 9) containing Cα sequences and lacking J sequences. These two fragments (der 14 and 14q32 in FIG. 9) were cloned from a genomic library constructed from U-266 DNA along with a normal 14q 32 locus (14q32 germline in FIG. 9). In order to determine whether a gene was located in proximity to the chromosomal breakpoints in der 14, the 2.5 BE restriction fragment (see FIG. 9), which was at the opposite side of the Ig Cα sequences, was used to probe a Northern blot carrying RNA from various MM cell lines. The results (FIG. 10) showed that a 1.9 kb mRNA was detectable in some of these cell lines including U-266. This result showed that a gene, called MUM2, normally not present within the Ig locus on chromosome 14q32, had been translocated in proximity of the Ig locus in U-266 cells. Since the Ig locus contains strong transcriptional regulatory elements, it is likely that the expression of this gene is deregulated in these cells. The structure of the MUM2 gene and its protein are currently under investigation. The 2.5 BE probe and other probes derived from the der 14 phage can be used to screen MM cases for MUM2 rearrangements as shown for MUM1 (FIG. 7).

Experimental Discussion

Figure 11A:
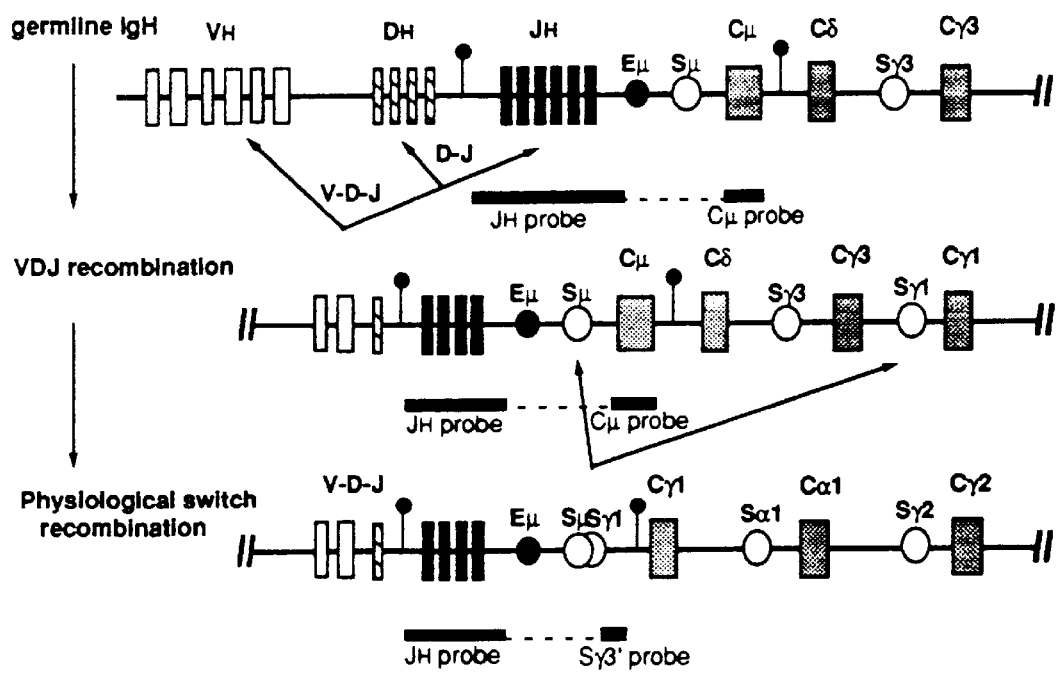
FIGS. 11A–B. Schematic representation of IgH DNA rearrangements in normal B cells and in tumors carrying chromosomal translocations breaking the S region of the IgH locus. Note that in physiological IgH rearrangements (FIG. 11A) JH sequences and C sequences (Cµ before and Cγ after switch recombination, respectively) are consistently found within the same BamHI restriction fragment. Conversely, JH and C sequences are not linked, and are present on two different chromosomes [derivative X and derivative 14(14q+)] in cells carrying a chromosomal translocation breaking the switch region (FIG. 11B)
Figure 11B:
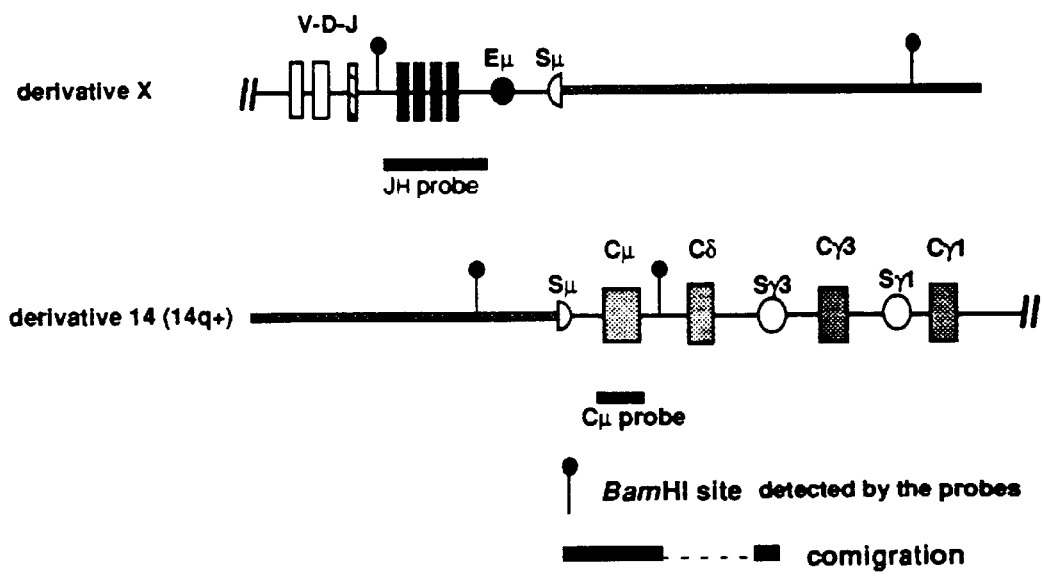
Figure 12A:
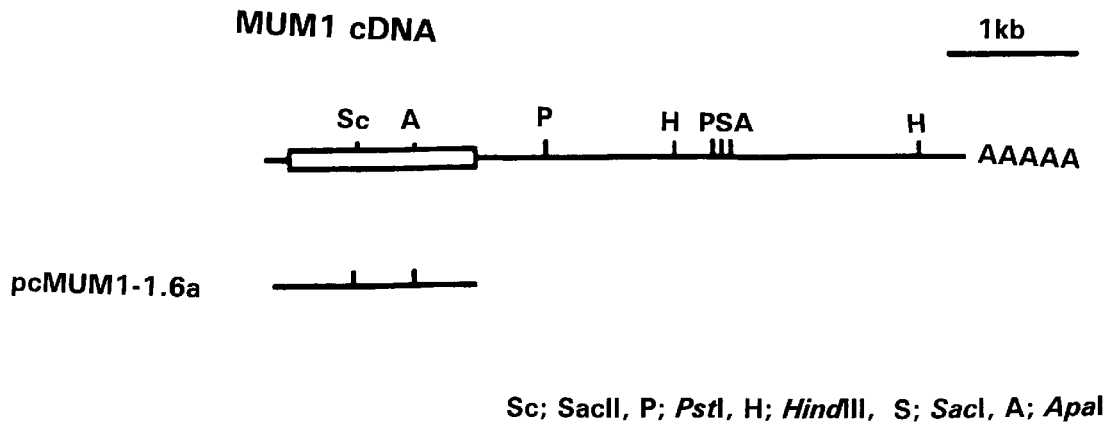
FIGS. 12A–B. MUM1 cDNA. cDNA insert is cloned into EcoRI/BamHI site of the pBluescript KS+. Bacteria strain used is DH5α cells. pcMUM1.16a contains full length open reading frame of nt. 217–1572.
Figure 12B:
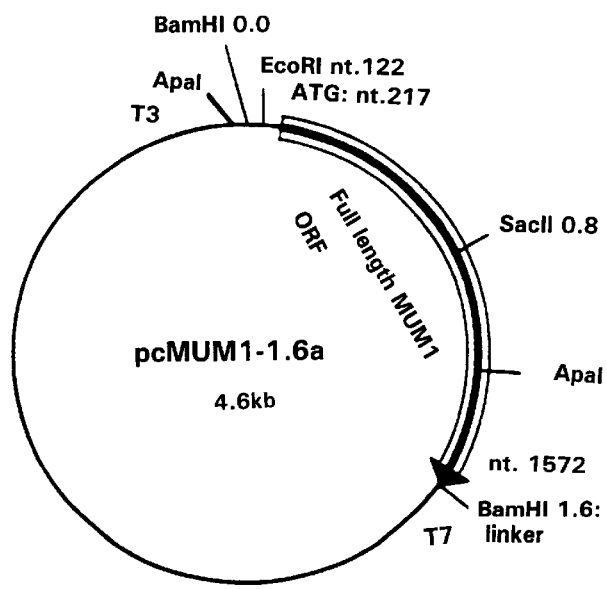
Figure 13:
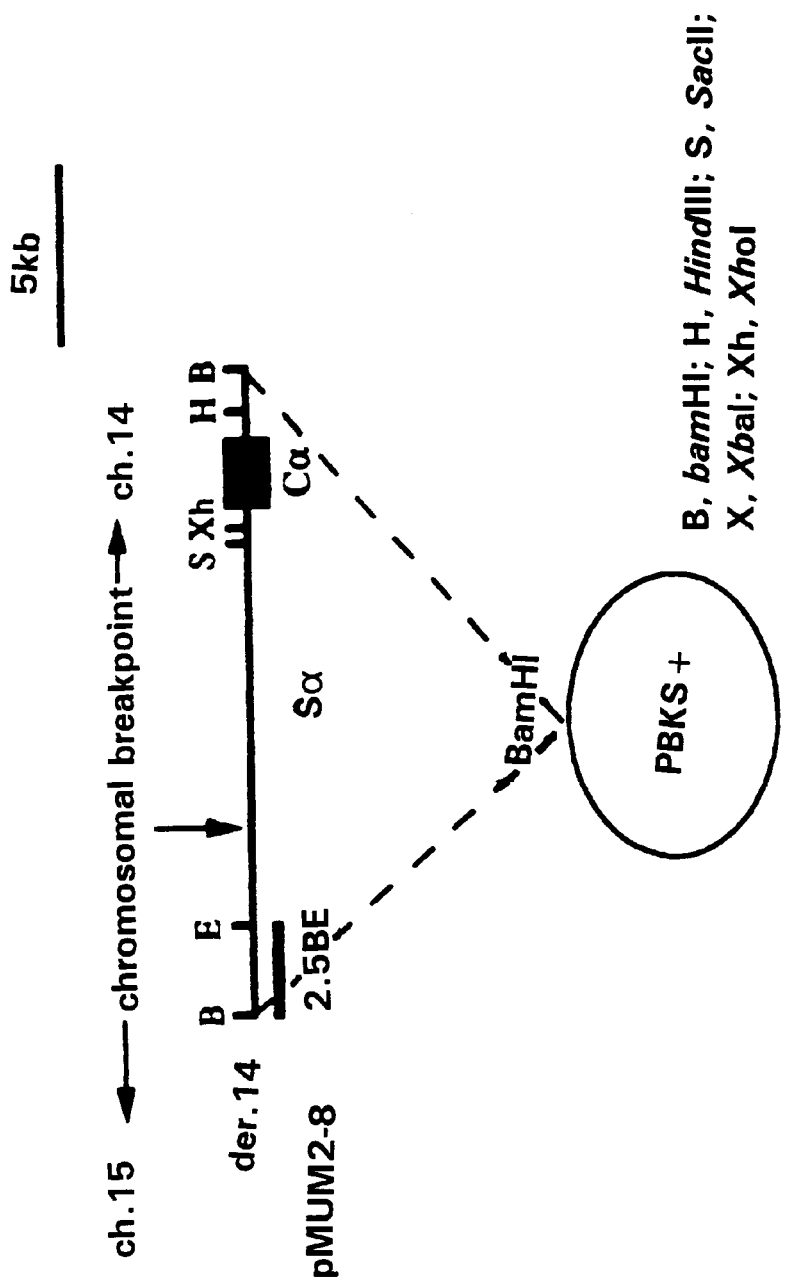
FIG. 13. Breakpoint Cloning of the U-266 Cell Line. pMUM2-8 has a 22.0 KB insert in BamHI site of pBluescript KS+.

Using the experimental strategies used for the identification of the MUM1 and MUM2 genes in the SK-MM-1 and U-266 cell lines, respectively, it is possible to analyze most MM cases and isolate the corresponding genes. The scheme shown in FIG. 11 shows that the physiological IgH gene rearrangements (FIG. 11A) typically maintain linkage of C and J sequences and this linkage becomes detectable by using an appropriate restriction enzyme digestion (BamHI in the example in FIG. 11). Conversely, chromosomal translocations (14q+) affecting the IgH locus on 14q32 lead to breakage of the C-J linkage and the two sets of sequences appear on distinct restriction fragments. (FIG. 11B) Table 1 shows the application of this analysis to a panel of MM cell lines and biopsies. The results show that at least 65% of cases show breakage of the C-J linkage within Ig J or switch regions. The restriction fragments containing either C or J sequences (R in Table 1) can be cloned as shown for the SK-MM-1 and U-266 cell lines and the genes flanking the chromosomal breakpoints can be used as probes to screen additional MM cases for similar rearrangements, whereas the sequence of the genes can be used to understand the consequences of these genetic lesions in multiple myeloma. Cloning of the chromosomal breakpoints and corresponding genes is currently ongoing for all of the MM cases shown in Table 1.

The method of analysis of 14q+ chromosomal translocations and identification of the genes altered in multiple myeloma of this invention will allow 1) the determination of chromosomal sequences involved in 14q+ translocations, the most important cytogenetic lesion associated with MM pathogenesis elucidation; 2) elucidation of specific gene lesions for MM; 3) a diagnostic method based on gene/DNA lesion and 4) a therapeutic approach aimed at counteracting the action of abnormal gene products.

TABLE 1

Summary of JH-C breakage analysis in MM cell lines and biopsies (cases). Rearrangement (R) involving physiologic Ig recombinations, i.e. retaining JH-C linkage are marked as R*; rearrangements lacking JH-C linkage, and therefore suggesting a 14q+ chromosomal breakpoint, are marked as R. The latter represents candidates for cloning an further analysis.

| Cell Line/Case | sIg | JH | Cμ | Cα | Sγ3' | possible breakpoint locus |
|---|---|---|---|---|---|---|
| RPMI-8226 | λ | D/D | D/D | G | R/G | Sγ |
| U-266 | Eλ | R/D | D/D | R/R/G | G | Sα |
| EJM | Gλ | R/R* | D/D | G | R*/G | JH~Sμ |
| XG-1 | Aκ | R*/D | D/D | R* | G | ND |
| XG-2 | Gλ | R*/D | D/D | G | R*/G | ND |
| XG-4 | Gκ | R*/R | D/D | G | R*/G | JH~Sμ |
| XG-5 | λ | R/D | D/D | G | G | JH~Sμ |
| XG-6 | Gλ | R*/R | D/D | G | R*/G | JH~Sμ |
| XG-7 | Aκ | R/D | D/D | R/G | R/D | Sγ |
| XG-10 | G | R*/R | D/D | G | R*/G | JH~Sμ |
| SK-MM-1 | κ | R*/R | R/D | G | R*/G | JH~Sμ |
| CASE125 | | R* | G | G | R* | ND |
| CASE33 | | R/R* | G | G | R/R* | Sγ |
| CASE34 | | R* | G | R* | G | ND |
| CASE93 | | R* | G | R* | G | ND |
| CASE91 | | R* | R* | R | G | Sα |
| CASE128 | | R* | G | R* | G | ND |

R*, comigrated bands with JH;
R, target bands to isolate;
ND, not determined
Possible breakage in switch regions:
Cell Lines 4/11 (36%)
Cases 2/6 (33%) Total 6/17 (35%)
Possible breakage in JH ~ switch regions:
Cell Lines 9/11 (82%)
Cases 2/6 (33%) Total 11/17 (65%)

References

1. Rabbitts, T. H. Chromosomal translocations in human cancer. Nature 372:143–149, 1994.
2. Dalla-Favera, R., Bregni, M., Erickson, D., Patterson, D., Gallo, R. C., Croce, C. M. Human c-myc oncogene is located on the region of chromosome 8 that is translocated in Burkitt lymphoma cells. Proc Nat Acad Sci USA 79:7824, 1982.
3. Tsujimoto, Y., Jaffe, E., Cossman, J., Gorham, J., Nowell, P. C., Croce, C. M. Clustering of breakpoints on chromosome 11 in human B-cell neoplasms with the t(11;14) chromosome translocation. Nature 315:340–343, 1985.
4. Motokura, T., Bloom, T., Kim, H. G., Juppner, H., Ruderman, J. V., Kronenberg, H. M., Arnold, A. A novel cyclin encoded by a bcl-1 linked candidate oncogene. Nature 350:512–515, 1991.
5. Tsujimoto, Y., Yunis, J., Onorato-Showe, L., Erikson, J., Nowell, P. C., Croce, C. M. Molecular cloning of chromosomal breakpoint of B-cell lymphomas and leukemias with the t(11;14) chromosome translocation. Science 224:1403–1406, 1984.
6. Cleary, M. L., Sklar, J.: Nucleotide sequence of a t(14;18) chromosomal breakpoint in follicular lymphoma and demonstration of a breakpoint-cluster region near a transcriptionally active locus on chromosome 18. Proc Natl Acad Sci USA 82: 7439, 1985.
7. Bakhshi, A., Jensen, J. P., Goldman, P., Wright, J. J., McBride, O. W., Epstein, A. L., Korsmeyer, S. J. Cloning the chromosomal breakpoint of t(14;18) human lymphomas: clustering around JH on chromosome 14 and near a transcriptional unit on 18. Cell 41:889, 1985.
8. Ye, B. H., Lista, F., Lo Coco, F., Knowles, D. M., Offit, K., Chaganti, R. S. K., Dalla-Favera, R. Alterations of a zinc finger-encoding gene, BCL-6, in diffuse large-cell lymphoma. Science 262:747–750, 1993.
9. Dewald, G. W., Kyle, R. A., Hicks, G. A., Greipp, P. R. The clinical significance of cytogenetic studies in 100 patients with multiple myeloma, plasma cell leukemia, or amyloidosis. Blood 66:380–390, 1985.
10. Gould, J., Alexanian, R., Goodacre, A., Pathak, S., Hecht, B., Barlogie, B. Plasma cell karyotype in multiple myeloma. Blood 71:453–456, 1988.
11. Weh, H. J., Gutensohn, K., Selbach, J., Kruse, R., Wacker-Backhaus, G., Seeger, D., Fiedler, W., Fett, W., Hossfeld, D. K. Karyotype in multiple myeloma and plasma cell leukemia. Eur J Cancer 29A:1269–1273, 1993.
12. Jernberg, H., Zech, L., Nilsson, K. Cytogenetic studies on human myeloma cell lines. Int J Cancer 40: 811–817, 1987.
13. Zhang, X-G., Gaillard, J. P., Robillard, N., Lu, Z-Y., Gu, Z-G., Jourdan M., Boiron, J. M., Bataille, R., Klein, B. Reproducible obtaining of human myeloma cell lines as a model for tumor stem cell study in human multiple myeloma. Blood 83:3654–3663, 1994.
14. Seto, M., Yamamoto, K., Iida, S., Akao, Y., Utsumi, K. R., Kubonishi, I., Miyoshi, I., Ohtsuki, T., Yawata, Y., Namba, M., Motokura, T., Arnold, A., Takahashi, T., Ueda, R. Gene rearrangement and overexpression of PRAD1 in lymphoid malignancy with t(11;14)(q13;q32) translocation. Oncogene 7:1401–1406, 1992.
15. Rabbitts, P. H., Douglas, J., Fisher, P., Nacheva, E., Karpas, A., Catovsky, D., Melo, J. V., Baer, R., Stinson, M. A., Rabbitts, T. H. Chromosome abnormalities at 11q13 in B cell tumours. Oncogene 3:99103, 1988.
16. Fiedler, W., Weh H. J., Hossfeld, D. K. Comparison of chromosome analysis and BCL-1 rearrangement in a series of patients with multiple myeloma. Br J Haematol 81: 58–61, 1992.
17. Taniwaki, M., Nishida, K., Takashima, T., Nakagawa, H., Fujii, H., Tamaki, T., Shimazaki, C., Horiike, S., Misawa, S., Kashima, K. Nonrandom chromosomal rearrangements of 14q32.3 and 19p13.3 and preferential deletion of lp in 21 patients with multiple myeloma and plasma cell leukemia. Blood 84: 2283–2290, 1994.
18. Sun, Z., Kitchingman, G. R. Sequencing of selected regions of the human immunoglobulin heavy-chain gene locus that completes the sequence from JH through delta constant region. DNA sequence 1:347–355, 1991.
19. Eton, O., Scheinberg, D. A., Houghton, A. N. Establishment and characterization of two human myeloma cell lines secreting kappa light chains. Leukemia 3: 729–735, 1989.
20. Mazars, G-R., Portier, M., Zhang, X-G., Jourdan, M., Bataille, R., Theillet, C., Klein, B. Mutations of the pS3 gene in human myeloma cell lines. Oncogene 7: 1015–1018, 1992.
21. Iida, S., Seto M., Yamamoto, K., Tojo, A., Asano, S., Kamada, N., Ariyoshi, Y., Takahashi, T., Ueda, R. MLLT3 gene on 9p22 involved in t(9;11) leukemia encodes a serine/proline rich protein homologous to MLLT1 on 19p13. Oncogene 8(11): 3085–3095, 1993.
22. Rao, P. H., Murty, V. V. S., Gaidano, G., Hauptschein, R., Dalla-Favera, R., and Chaganti, R. S. K. Subregional mapping of 8 single copy loci to chromosome 6 by fluorescence in situ hybridization. Cytogenet. Cell Genet. 66:272–273, 1994.
23. Kozak, M. The scanning model for translation: an update. J. Cell. Biol. 108:229–241, 1989.

24. Driggers, P. H., Ennist, D. L., Gleason, S. L., Mak, W-H., Marka, M. S., Levi, B-Z., Flanagan, J. R., Appella, E., Ozato, K.: Proc Natl Acad Sci USA 87: 3743–3747, 1990.
25. Veals, S. A., Schindler, C., Leonardo, D., Fu, X-Y., Aebersold, R., Darnell, J. E., Levy, D. E. Subunit of an alpha-interferon-responsive transcription factor is related to interferon regulatory factor and myb families of DNA-binding proteins. Mol Cell Biol 12: 3315–3324, 1992.
26. Grant, C. E., Vasa, M. Z., Deeley, R. G. cIRF-3, a new member of the interferon regulatory factor (IRF) family that is rapidly and transiently induced by dsRNA. Nucleic Acid Res 23:2137–2145, 1995.
27. Matsuyama, T., Grossman, A., Mittrucker, H-W., Siderovski, D. P., Kiefer, F., Kawakami, T., Richardson, C. D., Taniguchi, T., Yoshinaga, S. K., Mak, T. W. Molecular cloning of LSIRF, a lymphoid-specific member of the interferon regulatory factor family that binds the interferon-stimulated response element(ISRE). Nucleic Acid Res 23:2127–2136, 1995.
28. Eisenbeis, C. F., Singh, H., Storb, U. Pip, a novel IRF family member, is a lymphoid-specific, PU.1-dependent transcriptional activator. Genes & Dev 9:1377–1387, 1995.
29. Yamagata, T., Nishida, J., Tanaka, T., Sakai, R., Mitani, K., Yoshida, M., Taniguchi, T., Yazaki, Y., Hirai, H. A novel interferon regulatory factor family transcription factor, ICSAT/Pip/LSIRF, that negatively regulates the activity of interferon-regulated genes. Mol Cell Biol 16:1283–1294, 1996.

What is claimed is:

1. An isolated nucleic acid molecule encoding a MUM-1 protein having the amino acid sequence shown in FIGS. 5B-1–5B-3 (SEQ. ID NO 14).

2. The isolated nucleic acid molecule of claim 1, wherein the nucleic acid molecule is a DNA molecule.

3. The isolated DNA molecule of claim 2, wherein the DNA molecule is a cDNA molecule.

4. The isolated DNA molecule of claim 3, wherein the DNA molecule is a cDNA molecule having the nucleotide sequence shown in FIG. 5B (SEQ. ID NO 13).

5. The isolated nucleic acid molecule of claim 1, wherein the nucleic acid molecule is an RNA molecule.

6. The isolated nucleic acid molecule of claim 1 operatively linked to a promoter of RNA transcription.

7. A vector comprising the nucleic acid molecule of claim 1.

8. A vector comprising the nucleic acid molecule of claim 3.

9. The vector of claim 8, wherein the vector is a plasmid.

10. The plasmid of claim 9, designated pcMUM1-1.6a (ATCC Accession No. 97579).

11. The plasmid of claim 9, designated pMUM1-2.4B/N (ATCC Accession No. 97578).

12. The plasmid of claim 9, designated pMUM1-7.7B (ATCC Accession No. 97577).

13. A host cell comprising the vector of claims 7, 8 or 9.

14. The host cell of claim 13, wherein the cell is selected from the group consisting of a bacterial cell; a plant cell; an insect cell; and a mammalian cell.

* * * * *